United States Patent
Tabuchi et al.

(10) Patent No.: US 7,410,559 B2
(45) Date of Patent: Aug. 12, 2008

(54) ELECTROPHORESIS METHODS

(75) Inventors: Mari Tabuchi, Tokushima (JP); Yoshinobu Baba, Tokushima (JP)

(73) Assignee: Japan Science and Technology Agency, Kawaguchi-Shi (JP)

( * ) Notice: Subject to any disclaimer, the term of this patent is extended or adjusted under 35 U.S.C. 154(b) by 245 days.

(21) Appl. No.: 10/479,245

(22) PCT Filed: May 29, 2001

(86) PCT No.: PCT/JP01/04510

§ 371 (c)(1),
(2), (4) Date: Dec. 1, 2003

(87) PCT Pub. No.: WO02/097421

PCT Pub. Date: Dec. 5, 2002

(65) Prior Publication Data

US 2004/0168917 A1    Sep. 2, 2004

(51) Int. Cl.
*G01N 27/447* (2006.01)
(52) U.S. Cl. .................................. 204/453; 204/451
(58) Field of Classification Search ......... 204/450–455, 204/601–605
See application file for complete search history.

(56) References Cited

U.S. PATENT DOCUMENTS

| | | | |
|---|---|---|---|
| 5,069,766 A | 12/1991 | Zhu et al. | 204/454 |
| 5,482,608 A | 1/1996 | Keely et al. | 204/452 |
| 5,688,775 A * | 11/1997 | Renn et al. | 514/54 |
| 6,375,817 B1 * | 4/2002 | Taylor et al. | 204/453 |
| 6,605,475 B1 * | 8/2003 | Taylor et al. | 436/180 |
| 2004/0094419 A1 * | 5/2004 | Ueda et al. | 204/451 |

FOREIGN PATENT DOCUMENTS

| | | |
|---|---|---|
| EP | 386925 A1 | 9/1990 |
| EP | 809103 A2 | 11/1997 |
| JP | 11023530 | 1/1999 |
| JP | 2000-81417 A | 3/2000 |

OTHER PUBLICATIONS

Hamase et al. ("Curdlan Gel as a Promising Support for Electrophoresis," Analytical Sciences, Oct. 1991, vol. 7, 811-812).*

(Continued)

*Primary Examiner*—Alex Noguerola
(74) *Attorney, Agent, or Firm*—Birch, Stewart, Kolasch & Birch, LLP

(57) ABSTRACT

A separation carrier comprising β-1,3-glucan and/or methyl cellulose; a running buffer comprising the separation carrier; a method of capillary electrophoresis or microchip electrophoresis, wherein a sample comprising macromolecular compounds is run in the presence of the running buffer; a method of capillary electrophoresis or microchip electrophoresis, comprising the step of injecting the sample by an electrical injection or application of pressure; and a method for analyzing macromolecular compounds by the method of capillary electrophoresis or microchip electrophoresis. According to the present invention, it is possible to achieve high resolution quickly. Therefore, the methods are useful in the High Through-put screening analysis of proteins or sugar chains in gene analysis, proteome analysis or glycome analysis, and applicable in medical diagnostic apparatuses and the elucidation of biological functions, mechanisms of onset of diseases, etc.

25 Claims, 17 Drawing Sheets

OTHER PUBLICATIONS

Hamase et al. ("Curdlan Gel as a Bioinert Support for the Electrophoresis of Biologically Active Proteins," Analytical Sciences, Apr. 1996, vol. 12, 273-275).*

JPO English language translation of Yoshihide (JP 2000-081417).*

English language translation of Masanori Ueda et al. DNA Analysis by Mcrofabricated Capillary Electrophoresis Devices, No. 9, Bio. High Molecular Symposium, The Society of Polymer Sciences, Japan, 1999, pp. 6-8.*

Tabuchi et al, Capillary Denki Eido ni yoru Tanpakushitsu no Kaiseki, Dai 20 kai Capillary Denki Eido Symposium Yoshishu, 2000, pp. 210-211.

Ueda et al, Microchip-ka Capillary Denki Eido-ho no yoru DNA Kaiseki, Dai 9 kai Bio Kou-Bunshi Symposium Yoshishu, 1999, pp. 74-75.

"Protein Analysis by Capillary Electrophoresis", Proceedings of the 20th Symposium on Capillary Electrophoresis, Published Nov. 29, 2000.

Fujii, et al., Analysis of Material Flow and Design of Zero-emission Technology in Production Process of Wakame, Kankyokagakukaishi, 2000, vol. 13, No. 5, pp. 586-592.

* cited by examiner

Migration Time (min)

Migration Time (min)

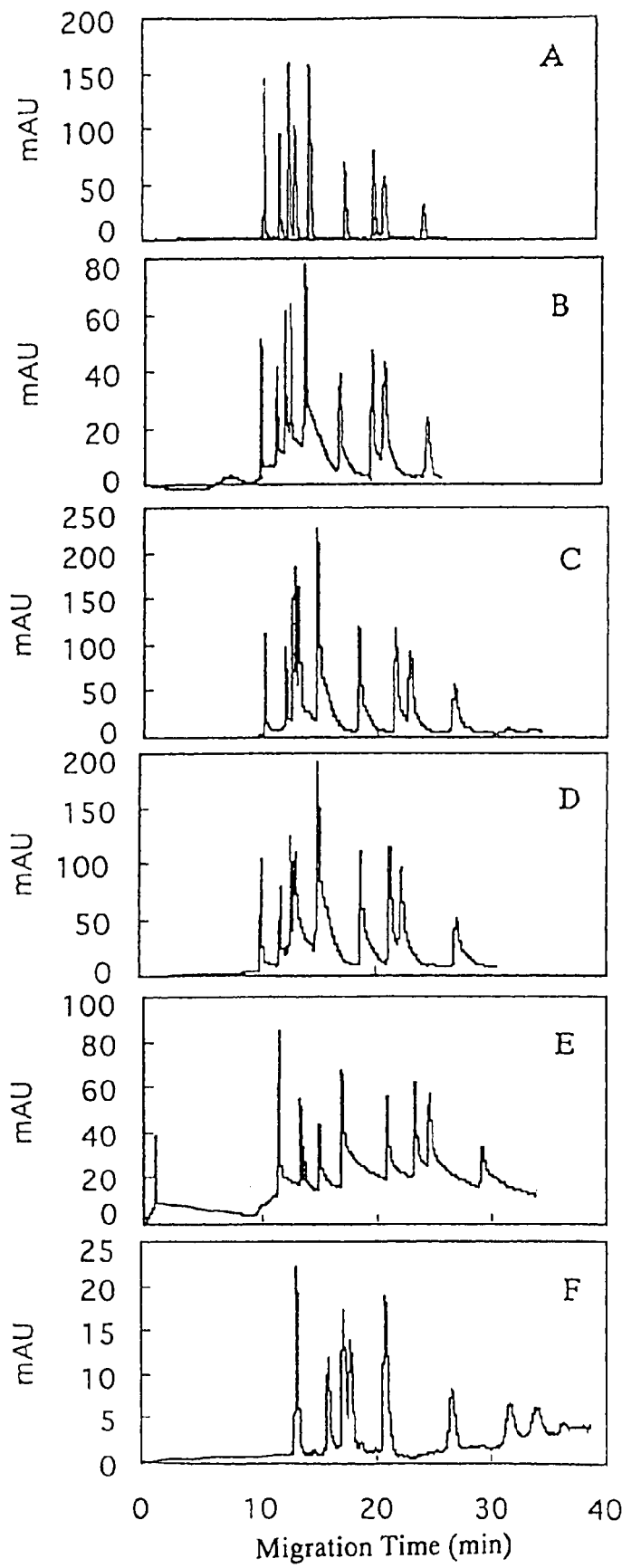

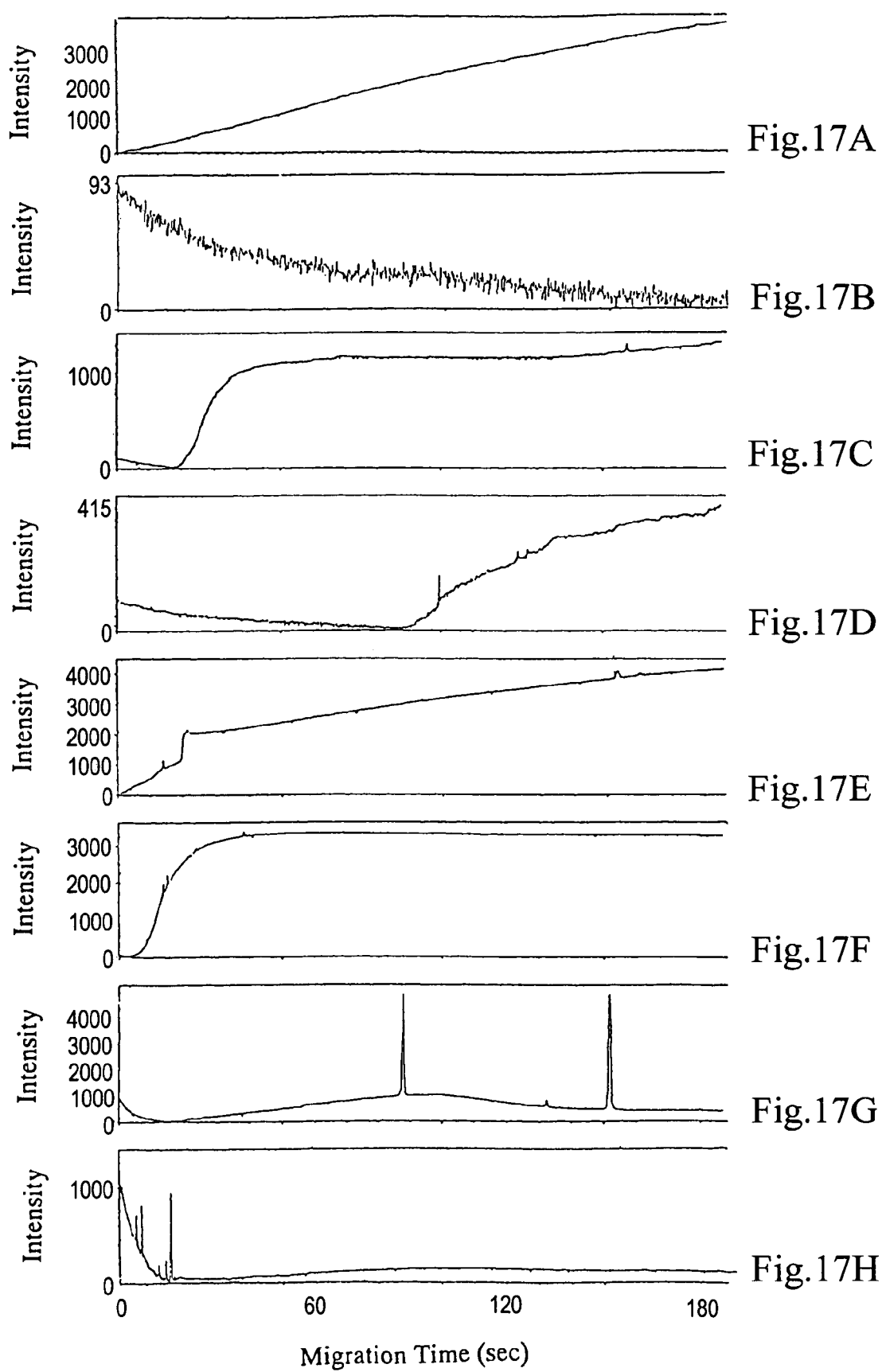

US 7,410,559 B2

ELECTROPHORESIS METHODS

This application claims priority of PCT application Ser. No. PCT/JP01/04510, filed on May 29, 2001.

TECHNICAL FIELD

The present invention relates to a method of electrophoresis and a method for analyzing macromolecular compounds, which are suitable for the electrophoresis of macromolecular compounds and by which high resolution can be achieved conveniently and quickly; and are applicable to gene analysis, proteome analysis, glycome analysis and the like. More specifically, the present invention relates to a separation carrier, a running buffer, a method of electrophoresis and a method for analyzing macromolecular compounds, by which macromolecular compounds such as proteins, peptides, amino acids, sugar chains, polysaccharides and nucleic acids (e.g., DNA, RNA) can be separated quickly at high resolution.

BACKGROUND ART

With human genome analysis, it has been expected that genome functions will be elucidated. Specifically, it is expected that by transcriptome analysis, proteome analysis, metabolome analysis, glycome analysis, etc., for example, expression of transcription products based on nucleotide sequence information and functions of gene products (proteins), in vivo metabolites, sugar chains, etc., will be elucidated to thereby elucidate the mechanisms of onset of diseases. Additionally, by the elucidation of the mechanisms of onset of diseases, applications to the prevention, treatment, etc. of such diseases are expected.

Currently, regarding proteome analysis, for example, profiling of protein by two-dimensional electrophoresis, etc. are conducted. However, the aforementioned two-dimensional electrophoresis has drawbacks such that the procedures are complicated, that long operating time is required, and that large volume of sample is required.

Additionally, in some cases, capillary electrophoresis and microchip electrophoresis may be used to analyze proteins or sugar chains. However, when analyzing a protein by the capillary electrophoresis or microchip electrophoresis, since the protein may be adsorbed in some cases to the capillary. Therefore, there is a drawback that the development thereof may be interfered, which makes it difficult to analyze it.

Furthermore, since conventional electrophoresis has a limitation as to shortening the separation time in order to achieve high-speed separation, electrophoresis is conducted under high voltage. However, there is a drawback of reduced resolution due to the high voltage exerted in some cases.

Accordingly, there is a need for the establishment of techniques for High Through-put screening analysis of macromolecular compounds, specifically, proteins and sugar chains, of which operations are simple and by which high resolution can be obtained quickly.

DISCLOSURE OF INVENTION

An object of the present invention is to provide a separation carrier, a running buffer and a method of electrophoresis, capable of analyzing macromolecular compounds such as proteins, peptides, amino acids, sugar chains, polysaccharides and nucleic acids (e.g., DNA, RNA, etc.), which are suitable for the electrophoresis of macromolecular compounds, and of which operations are simple and by which high resolution can be obtained quickly, as well as a method for analyzing such macromolecular compounds based on the method of electrophoresis.

Specifically, the gist of the present invention relates to:

[1] a separation carrier usable for capillary electrophoresis or microchip electrophoresis, wherein the separation carrier comprises one kind of compound selected from the group consisting of β-glucan and methyl cellulose;

[2] the separation carrier described in item [1] above, wherein the separation carrier comprises as the β-glucan at least one kind selected from the group consisting of laminaran containing β-1,3-glucan, curdlan containing β-1,3-glucan, a plant extract containing β-1,3-glucan, a seaweed extract containing β-1,3,3-glucan, an yeast extract containing β-1,3,3-glucan, a fungal extract containing β-1,3-glucan, and a fungal cultured medium containing β-1,3-glucan;

[3] the separation carrier described in item [1] above, wherein the separation carrier comprises a seaweed extract containing β-1,3-glucan as the β-glucan;

[4] the separation carrier described in item [3] above, wherein the seaweed extract is an extract obtained by subjecting raw material seaweed to one kind of extraction method selected from the group consisting of a water extraction, an acid/alkali extraction and a solvent extraction;

[5] a running buffer usable for capillary electrophoresis or microchip electrophoresis, wherein the running buffer comprises the separation carrier of any one of items [1] to [4] above;

[6] the running buffer described in item [5] above, wherein the running buffer is one kind of buffer selected from the group consisting of the following (1) to (3):

(1) a buffer comprising a phosphate buffer at pH 1.0 to 12.0 at a concentration of 1 mM to 0.5 M;

(2) a buffer comprising a borate buffer at pH 5.0 to 11.0 at a concentration of 1 mM to 0.5 M; and (3) a buffer comprising a Tris-borate buffer at pH 5.0 to 11.0 at a concentration of 1 mM to 0.5 M, and wherein the running buffer comprises methyl cellulose at a concentration of 0.001 to 0.5% by weight;

[7] the running buffer described in item [5] above, wherein the running buffer is one kind of buffer selected from the group consisting of the following (1) to (4):

(1) a buffer comprising a phosphate buffer at pH 1.0 to 12.0 at a concentration of 1 mM to 0.5 M;

(2) a buffer comprising a borate buffer at pH 5.0 to 11.0 at a concentration of 1 mM to 0.5 M;

(3) a buffer comprising a Tris-borate buffer at pH 5.0 to 11.0 at a concentration of 1 mM to 0.5 M; and (4) a buffer further comprising 0.001 to 1.0% by weight of methyl cellulose in the buffer of the above item (3), and wherein the running buffer comprises curdlan at a concentration of 0.000001 to 0.1% by weight;

[8] the running buffer described in item [5] above, wherein the running buffer is one kind of buffer selected from the group consisting of the following (1) to (4):

(1) a buffer comprising a phosphate buffer at pH 1.0 to 12.0 at a concentration of 1 mM to 0.5 M;

(2) a buffer comprising a borate buffer at pH 5.0 to 11.0 at a concentration of 1 mM to 0.5 M;

(3) a buffer comprising a Tris-borate buffer at pH 5.0 to 11.0 at a concentration of 1 mM to 0.5 M; and (4) a buffer further comprising 0.001 to 1.0% by weight of methyl cellulose in the buffer of the above item (3), and wherein the running buffer comprises a seaweed extract at a concentration of 0.000001 to 0.1% by weight;

[9] a method of electrophoresis, characterized in that a sample comprising macromolecular compounds is run in capillary electrophoresis or microchip electrophoresis in the presence of the running buffer of any one of items [5] to [8] above;

[10] the method of electrophoresis described in item [9] above, wherein the macromolecular compounds are one kind selected from the group consisting of a protein, a peptide, an amino acid, a sugar chain, a polysaccharide and a nucleic acid;

[11] a method of electrophoresis, characterized by comprising the steps of injecting a sample comprising macromolecular compounds to a capillary, then applying pressure thereto, and then running the sample in an electric field for electrophoresis such that the macromolecular compound can be separated, in capillary electrophoresis;

[12] the method of electrophoresis described in item [11] above, wherein the macromolecular compounds are one kind selected from the group consisting of a protein, a peptide, an amino acid, a sugar chain, a polysaccharide and a nucleic acid;

[13] the method of electrophoresis described in item [11] or [12] above, comprising the steps:

(a) injecting a sample into a sample injection port of a capillary by application of pressure or an electrical injection, wherein the capillary comprises the sample injection port and an outlet, and the capillary is filled with a running buffer [hereinafter referred to as step (a)]; and (b) applying pressure and then running the sample [hereinafter referred to as step (b)] in capillary electrophoresis;

[14] the method of electrophoresis described in item [13], wherein the sample is injected into the capillary under the conditions of no water or no running buffer set in the outlet of the capillary in the step (a), and wherein pressure is applied to water or buffer in the step (b):

[15] the method of electrophoresis described in item [13] or [14], wherein the sample is injected into the capillary by an electrical injection at 1 to 30 kV for 1 to 30 seconds in the step (a), and wherein the sample is run in an electric field for electrophoresis of 20 V/cm to 10 kV/cm in the step (b);

[16] the method of electrophoresis described in item [13] or [14], wherein the sample is injected into the capillary by an electrical injection at 1 to 30 kV for 1 to 60 seconds in the step (a), and wherein a pressure of 2 to 50 mbar is applied for 2 to 30 seconds in the step (b);

[17] the method of electrophoresis according to any one of items [11] or [16] above, wherein the sample is run in the presence of the running buffer of any one of items [5] to [8] above;

[18] a method of electrophoresis, characterized by comprising the steps:

(A) using a microchip comprising a loading channel, a separation channel crossing the loading channel, a sample reservoir arranged at one end of the loading channel, and an outlet arranged at the other end of the loading channel, wherein the loading channel and the separation channel are filled with a running buffer, applying voltage or pressure to the loading channel, to supply a sample comprising macromolecular compounds from the sample reservoir, thereby introducing the sample into the separation channel [hereinafter referred to as step (A)]; and (B) applying pressure to the separation channel, and then running the sample [hereinafter referred to as step (B)];

[19] the method of electrophoresis described in item [18], wherein the macromolecular compounds are one kind selected from the group consisting of a protein, a peptide, an amino acid, a sugar chain, a polysaccharide and a nucleic acid;

[20] the method of electrophoresis described by item [18] or [19] above, wherein resolution is adjusted by controlling a degree of pressure applied in the step (B);

[21] the method of electrophoresis according to any one of items [18] to [20] above, wherein the sample is introduced into the separation channel by applying voltage to the loading channel under the conditions of no running buffer set in the outlet in the step (A); and wherein voltage is applied to the loading channel and the separation channel, thereby running the sample, in the step (B);

[22] the method of electrophoresis described in item [21] above, wherein a voltage of 10 to 500 V (loading voltage) is applied to the loading channel for 2 to 60 seconds in the step (A); and wherein a voltage of 10 to 500 V (squeezing voltage) is applied to the loading channel and, an electric field of 20 V/cm to 50 kV/cm is applied to the separation channel in the step (B);

[23] the method of electrophoresis according to any one of items [18] to [20] above, wherein the sample is introduced into the separation channel by applying pressure to the sample reservoir under the conditions of no running buffer set in the outlet in the step (A); and wherein pressure is applied to the separation channel and then the sample is run in step the (B);

[24] the method of electrophoresis described in item [23], wherein a pressure of 1 to 1520 mbar is applied to the sample reservoir in the step (A); and wherein a pressure of 1 to 1520 mbar is applied to the separation channel, and then an electric field of 20 V/cm to 50 kV/cm is applied thereto, in step the (B);

[25] the method of electrophoresis according to any one of items [18] to [24] above, wherein proteins having molecular weights of 9 to 205 kDa are separated within 15 seconds;

[26] the method of electrophoresis according to any one of items [18] to [24] above, wherein sugars comprising 2 to 100 monosaccharides as a constitutive sacccharide are separated within 15 seconds;

[27] the method of electrophoresis according to any one of items [18] to [24], wherein nucleic acids of 10 bases to 10 kilobases are separated within 50 seconds;

[28] a method for analyzing macromolecular compounds, characterized by comprising the steps of running a sample comprising macromolecular compounds by the method of electrophoresis of any one of items [9] to [27], thereby separating the macromolecular compounds; and measuring mobility by detecting the separated macromolecular compounds;

[29] the method for analyzing macromolecular compounds described in item [28] above, wherein the macromolecular compounds are one kind selected from the group consisting of a protein, a peptide, an amino acid, a sugar chain, a polysaccharide and a nucleic acid; and

[30] the method for analyzing macromolecular compounds described in item [28] or [29] above, wherein the separated macromolecular compounds are detected by at least one kind selected from the group consisting of a determination of UV wavelength light absorption, a fluorescence detection, an electrochemical detection and a chemiluminescence detection.

panel A, at 5 kV for 5 seconds during sample injection, running voltage 3.75 kV; panel B, at 5 kV for 5 seconds during sample injection, running voltage 6.5 kV; panel C, at 5 kV for 5 seconds during sample injection, running voltage 15 kV; panel D, at 8 kV for 8 seconds during sample injection, running voltage 10 kV; panel E, at 8 kV for 8 seconds during sample injection, running voltage 15 kV. Also, the following peaks appeared: 1, Bardykinin (MW: 1,060); 2, Angiotensin II (MW: 1,046); 3, α-Melanocyte stimulating hormone (MW: 1,665); 4, Thyrotropin releasing hormone (MW: 362); 5, Luteinizing hormone releasing hormone (MW: 1,182); 6, Leucine enkephalin (MW: 392); 7, Bombesin (MW: 1,620); 8, Methionine enkephalin (MW: 574); and 9, Oxytocin (MW: 1,007).

Figure 1A:
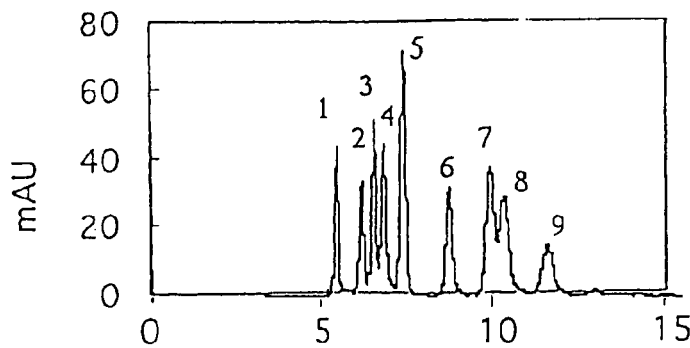
FIG. 1 shows the results obtained when optimal conditions for sample injection and optimal conditions for running voltage for the electrophoresis were studied in capillary electrophoresis. In the Figure, the individual panels are as follows.
Figure 1B:
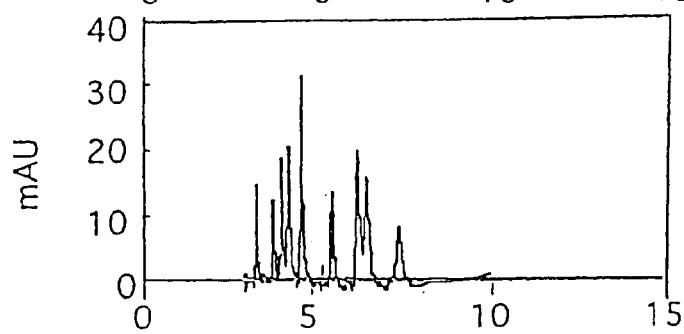
Figure 1C:
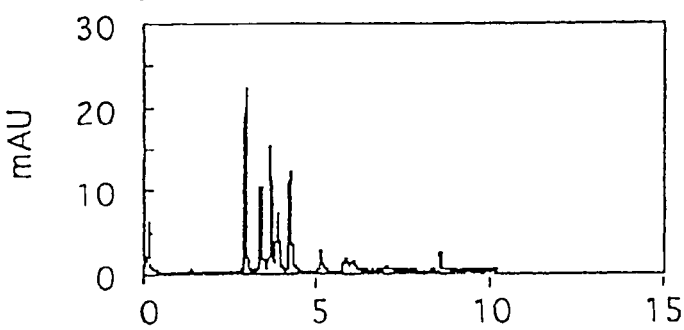
Figure 1D:
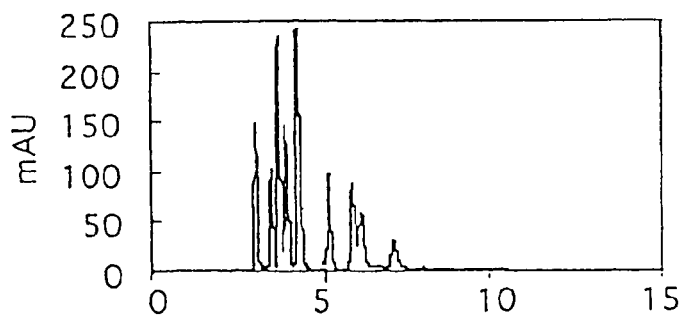
Figure 1E:
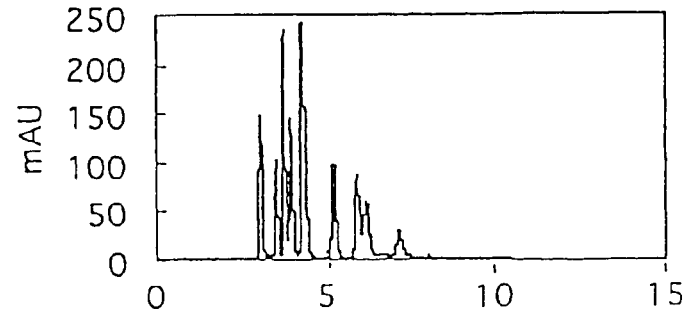
Figure 2A:
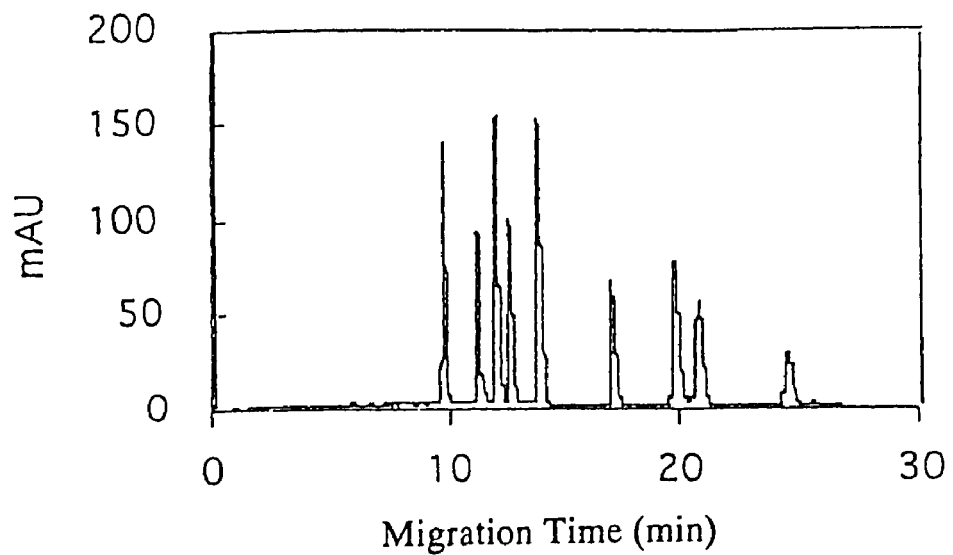
Figure 2B:
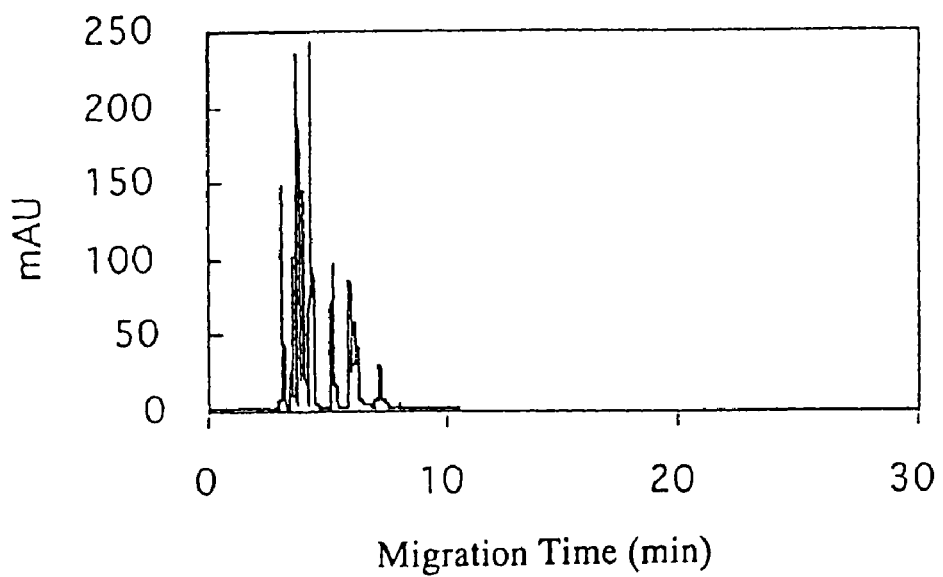

FIG. 2 shows the results of a comparison of the effects of a capillary of 24 cm in effective length and those of a capillary of 8.5 cm in effective length on migration time and resolution.

Figure 3A:
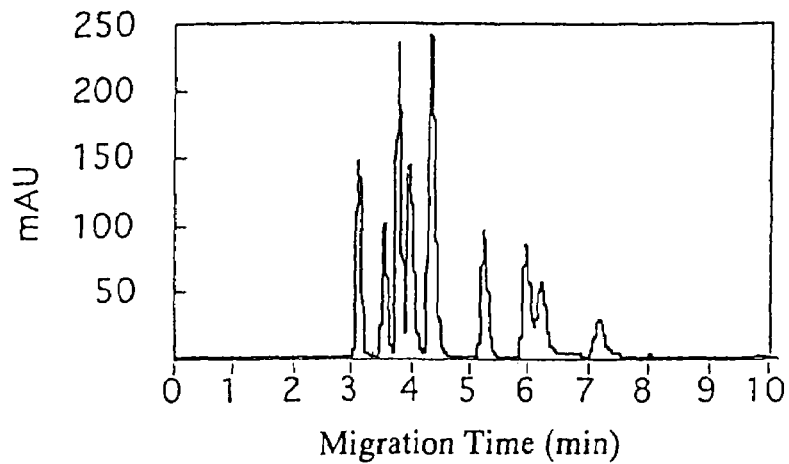
Figure 3B:
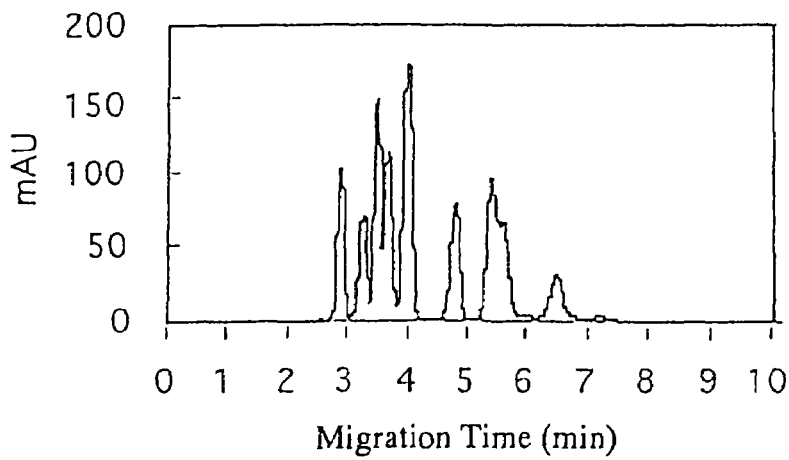
Figure 3C:
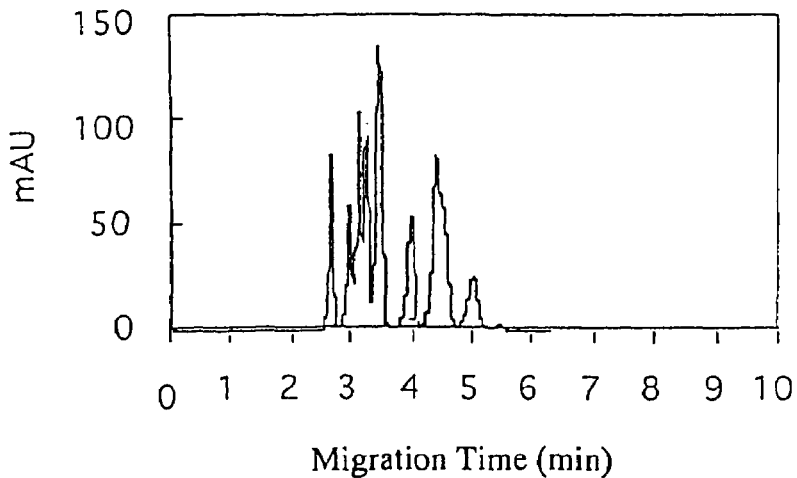
Figure 4A:
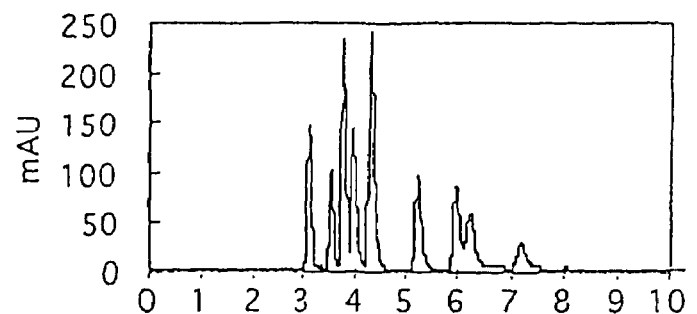
Figure 4B:
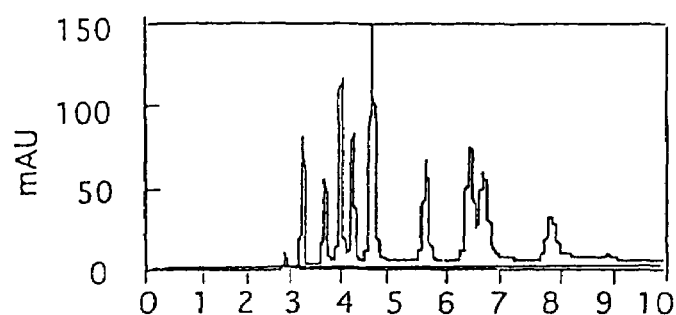
Figure 4C:
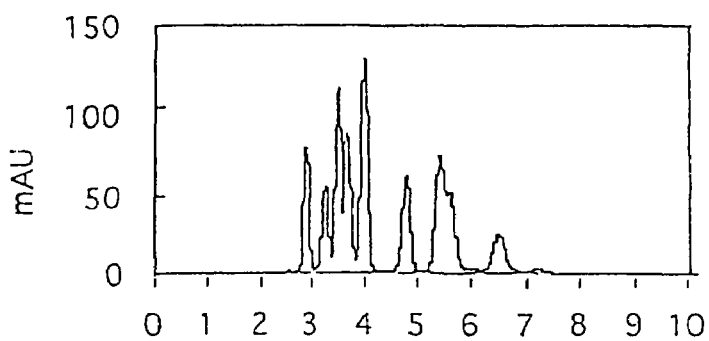
Figure 4D:
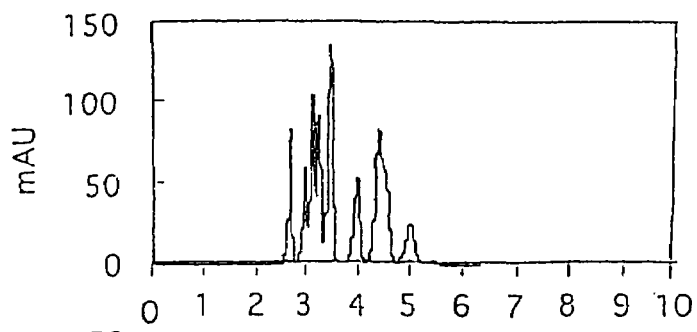
Figure 4E:
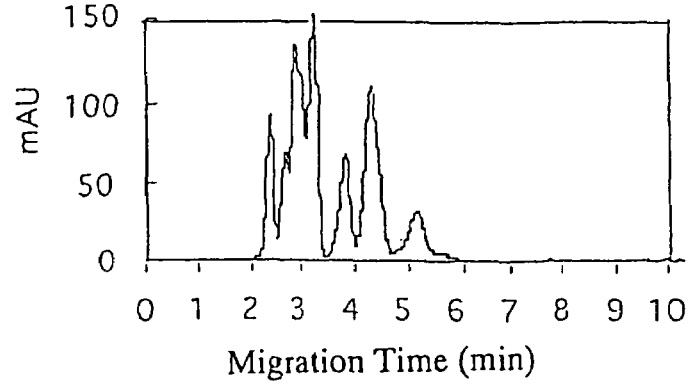

FIG. 3 shows the results of an examination of the effects of application of pressure on migration time after sample injection and prior to electrophoresis. The respective conditions for applying pressure are as follows: panel A, no application of pressure after sample injection; panel B, application of pressure after sample injection with the buffer set in the outlet; panel C, and application of pressure after sample injection, without the buffer set in the outlet.

FIG. 4 shows the results of a study on sample injection conditions. The sample was injected without setting the buffer in the outlet. The respective sample injection conditions are as follows: panel A, no application of pressure after sample injection; panel B, application of pressure at 10 mbar for 6 seconds after sample injection, sample injection port: water, outlet: no buffer; panel C, application of pressure at 10 mbar for 6 seconds after sample injection, sample injection port: water, outlet: water; panel D, application of pressure at 10 mbar for 8 seconds after sample injection, sample injection port: water, outlet: buffer; panel E, and application of pressure at 10 mbar for 7 seconds after sample injection, sample injection port: buffer, outlet: buffer.

Figure 5A:
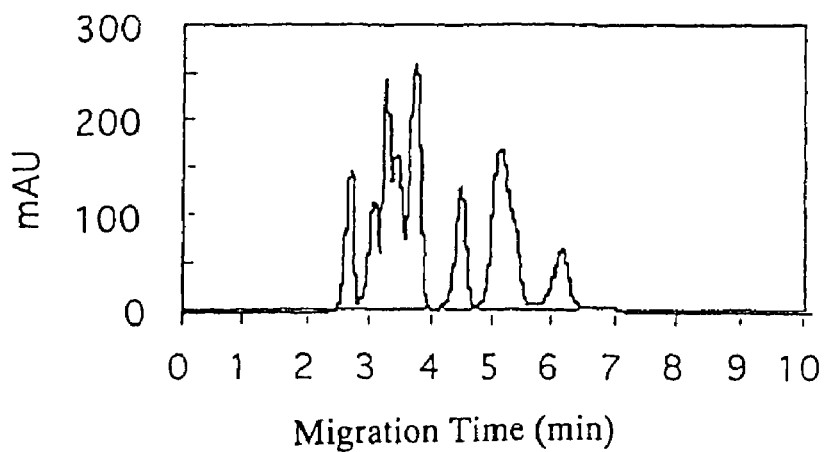
Figure 5B:
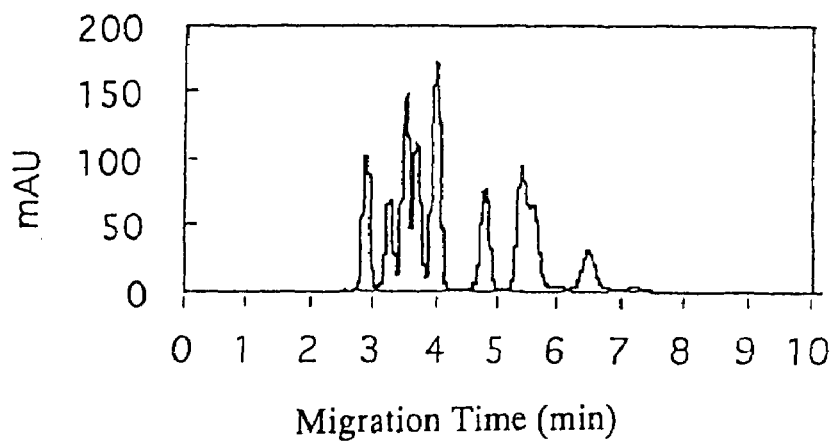
Figure 5C:
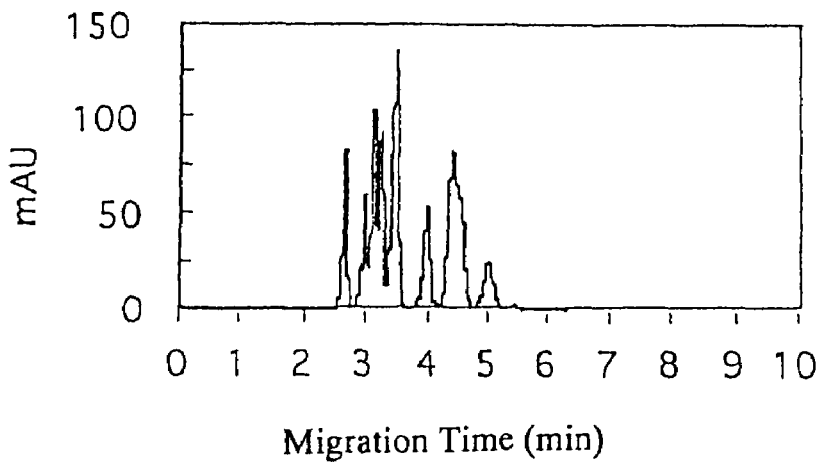

FIG. 5 shows the results of a study on the effects of time for applying pressure on migration time and resolution under the conditions in panel D in FIG. 4. The respective times for applying pressure are as follows: panel A, at 10 mbar for 2 seconds; panel B, at 10 mbar for 6 seconds; and panel C, at 10 mbar for 8 seconds.

Figure 6A:
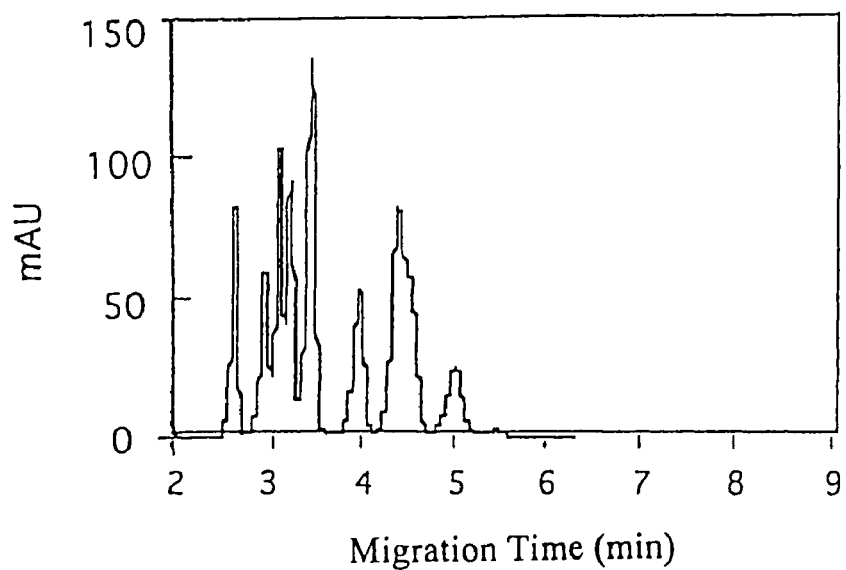
Figure 6B:
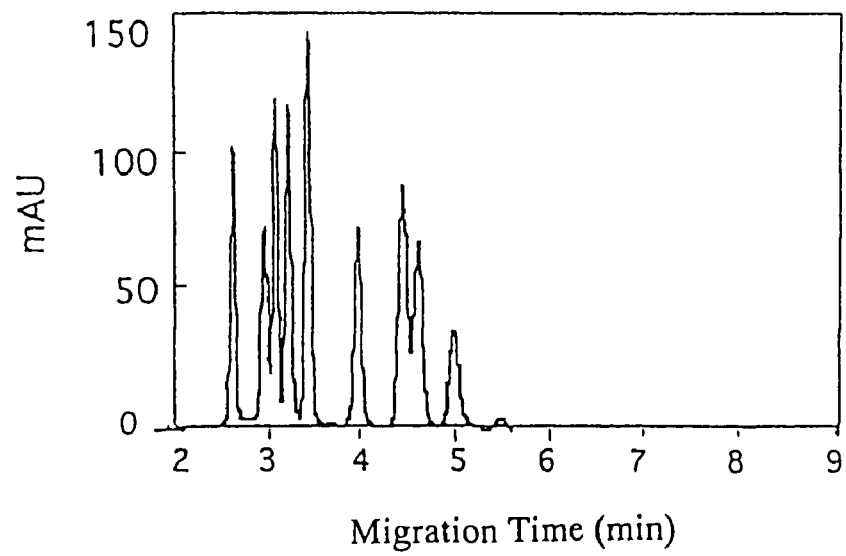

FIG. 6 shows the results of an examination of the effects of β-1,3-glucan (curdlan) on migration time and resolution using a system containing β-1,3-glucan (curdlan) as a separation carrier (final concentration 0.0001% by weight). Panel A shows the results obtained under the conditions without addition of curdlan, and Panel A' shows the results under the conditions with addition of curdlan.

Figure 7A:
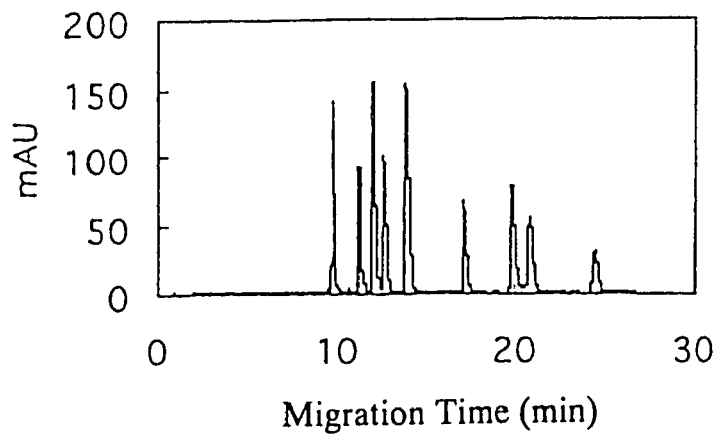
Figure 7B:
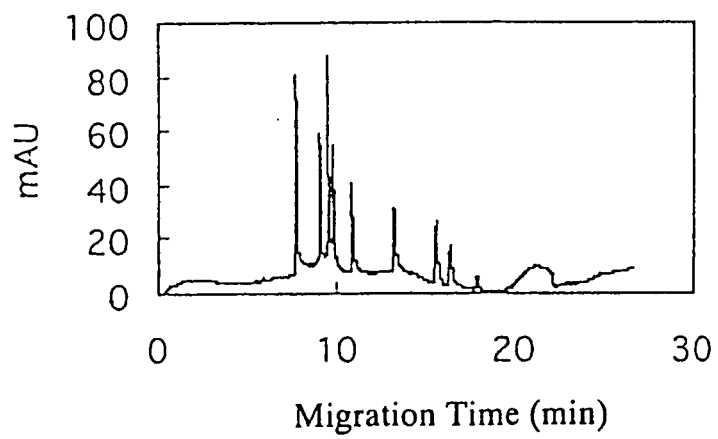
Figure 7C:
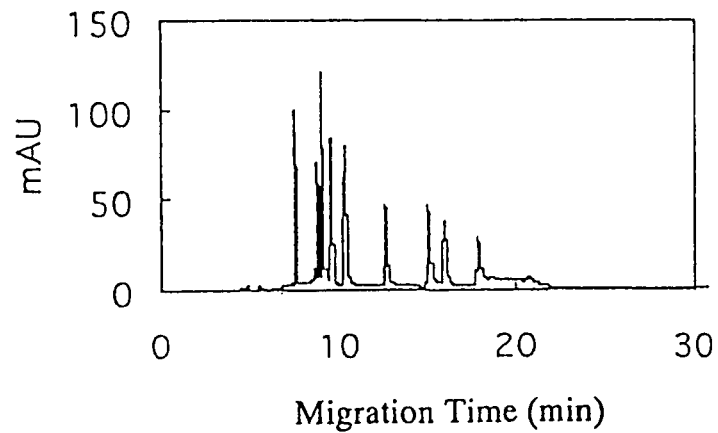
Figure 8A:
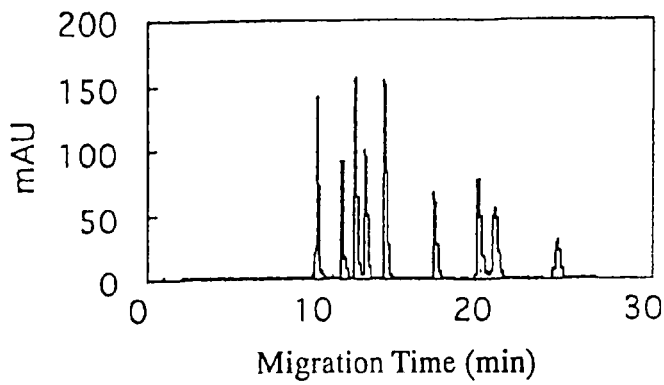
Figure 8B:
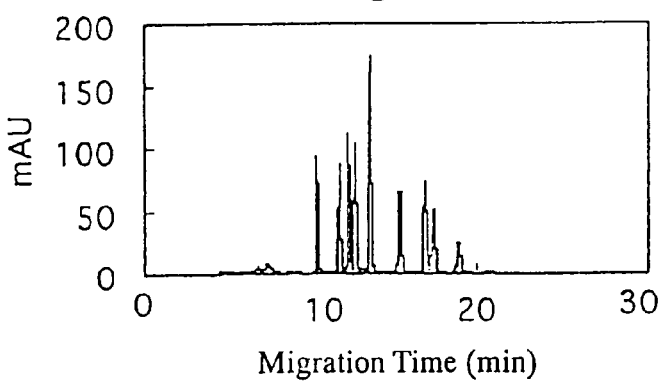
Figure 8C:
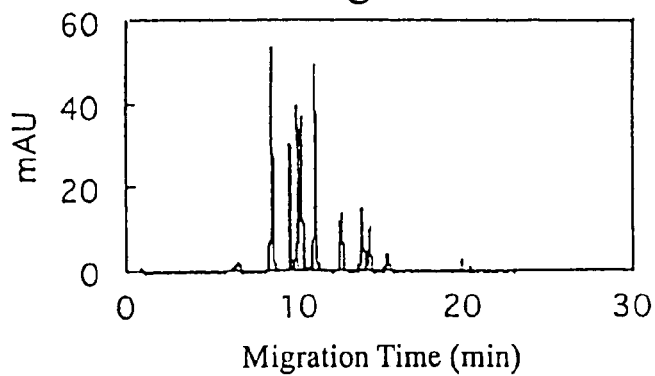
Figure 8D:
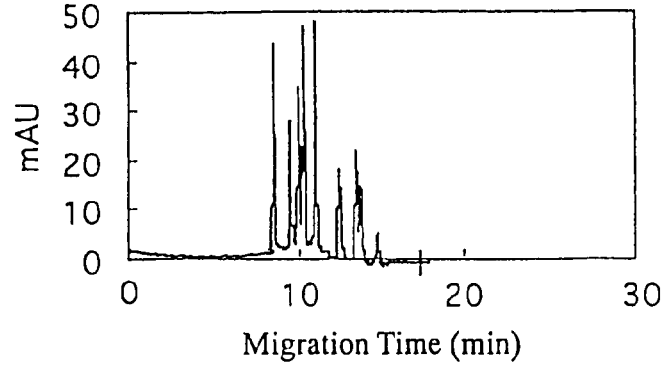

FIG. 7 shows the effects of the addition of methyl cellulose on migration time and resolution of peptide. Panel A: without addition of methyl cellulose, Panel B: with addition of 0.5% methyl cellulose, and Panel C: with addition of 0.1% methyl cellulose.

FIG. 8 shows the effects of the addition of polysaccharide on migration time and resolution of peptide. Panel A: without addition of polysaccharide, Panel B: with addition of 0.001% curdlan, Panel C: with addition of 0.0001% curdlan, and Panel D: with addition of 0.0001% seaweed extract.

FIG. 9 shows the effects of the addition of dextran on migration time and resolution of peptide. Panel A: without addition of dextran, Panel B: with addition of 0.5% dextran, Panel C: with addition of 1% dextran, Panel D: with addition of 5% dextran, Panel E: with addition of 10% dextran, and Panel F: with addition of 5% dextran. The dextran in panels A through E had an average molecular weight of approximately 100,000 to 200,000, and the dextran in panel F had an average molecular weight of approximately 60,000 to 90,000.

Figures 10A, 10B, 10C, 10D, 10E, 10F:
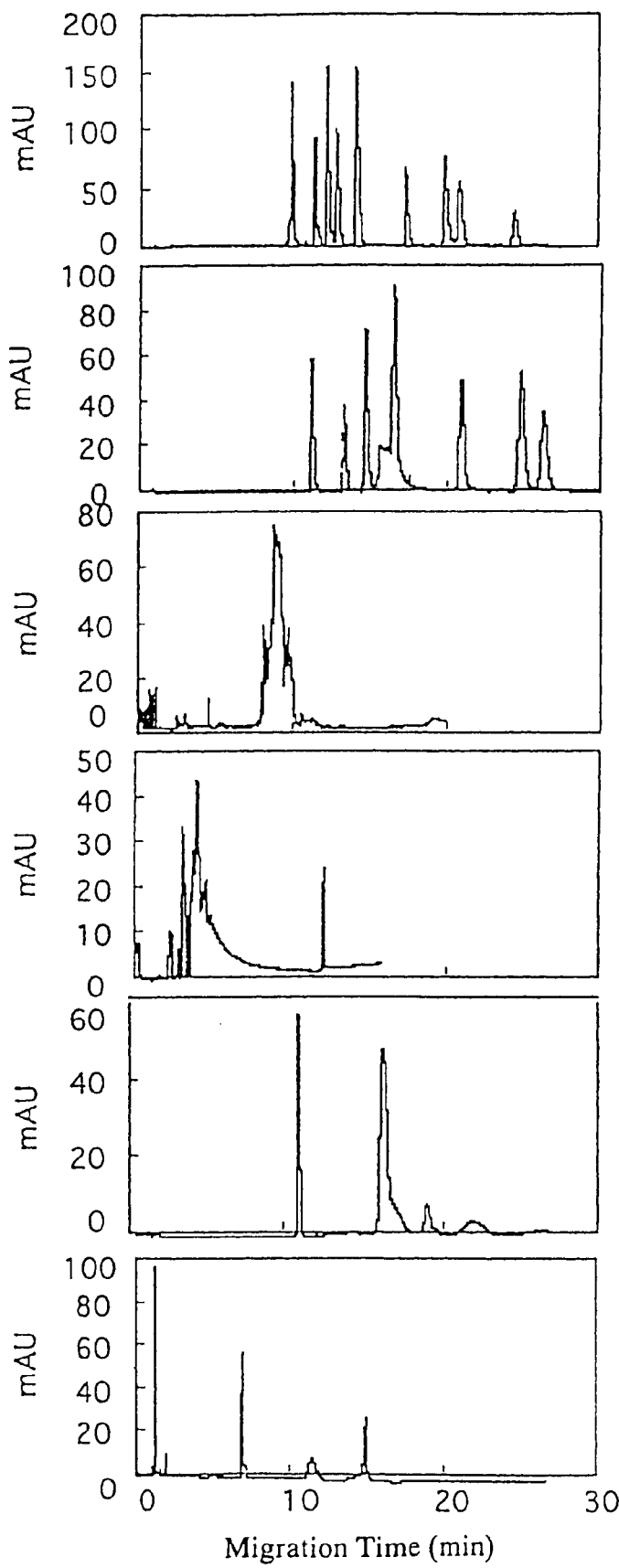

FIG. 10 shows the effects of the addition of SDS on migration time and resolution of peptide. Panel A: without addition of SDS, Panel B: with addition of 0.01% SDS, Panel C: with addition of 0.05% SDS, Panel D: with addition of, 0.1% SDS Panel E: with addition of 1% SDS ,and Panel F: with addition of 5% SDS.

Figure 11:
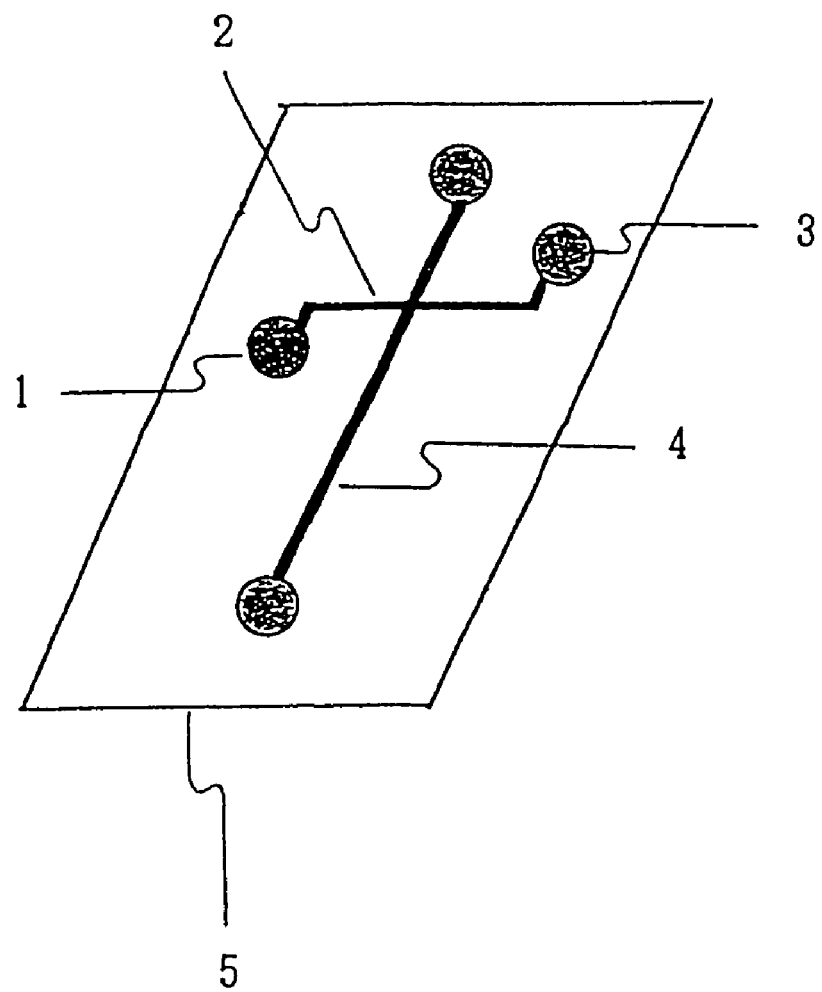
Figure 12A:
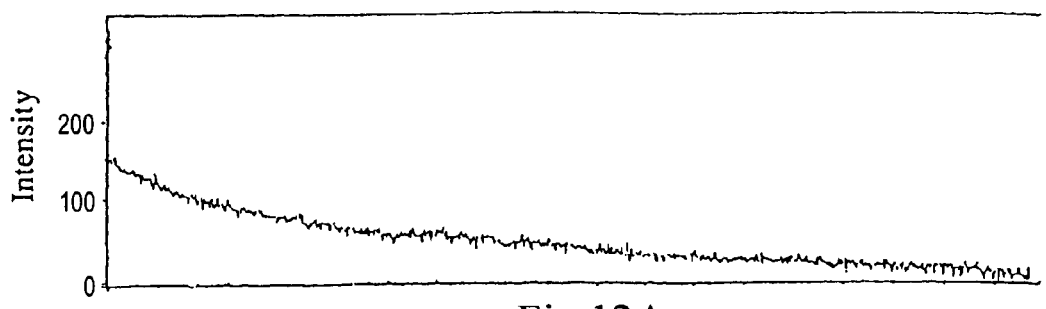
Figure 12B:
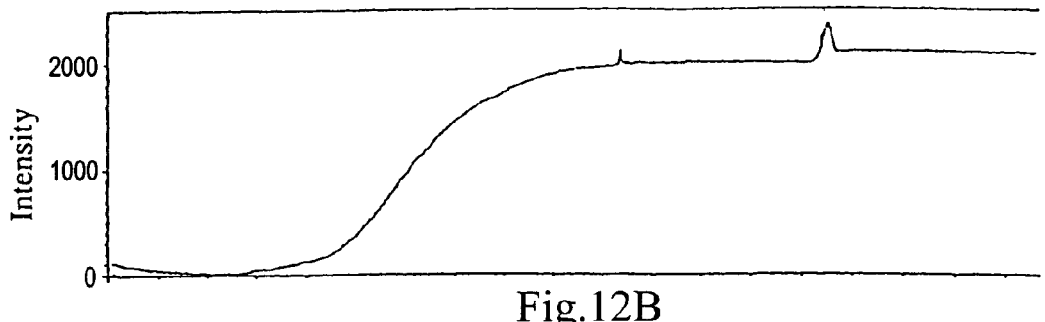
Figure 12C:
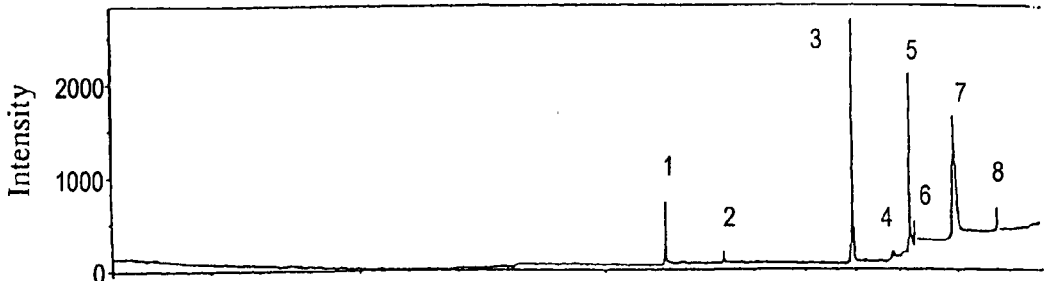
Figure 12D:
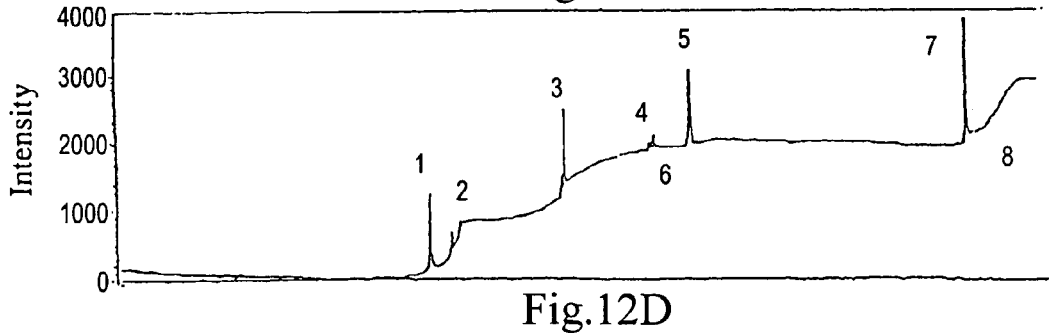
Figure 12E:
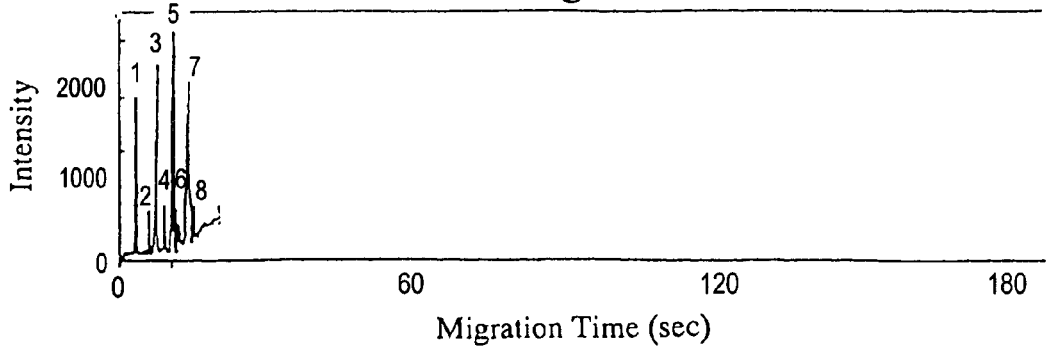

FIG. 11 shows an example of a microchip used for microchip electrophoresis. 1: sample reservoir, 2: loading channel, 3: outlet, 4: separation channel, and 5: microchip substrate.

FIG. 12 shows the results of a study on loading conditions and squeezing conditions in microchip electrophoresis. Panel A shows the results obtained when a low loading voltage (100 to 300 V), for 10 to 20 seconds, and a low squeezing voltage (100 to 400 V) were applied in conventional microchip electrophoresis. Panel B shows the results obtained when a high loading voltage (500 V), for 10 to 20 seconds, and a high squeezing voltage (500 V) were applied. Panel C shows the results obtained when a loading voltage of 100 V and a squeezing voltage of 100 V were applied and a pressure of 50 mbar was applied to the separation channel prior to electrophoresis, according to the aforementioned VP method. Panel D shows the results obtained when the sample was injected to the loading channel with application of pressure at 150 mbar and thereafter a pressure of 100 mbar was applied to the separation channel and a squeezing voltage (100 V) was applied, according to the aforementioned PP method. Panel E shows the results obtained when the sample was injected to the loading channel with application of pressure at 150 mbar and thereafter a pressure of 150 mbar was applied to the separation channel and a squeezing voltage (100 V) was applied, according to the aforementioned PP method. In all these cases, the electric field for electrophoresis was 267 V/cm.

Figure 13:
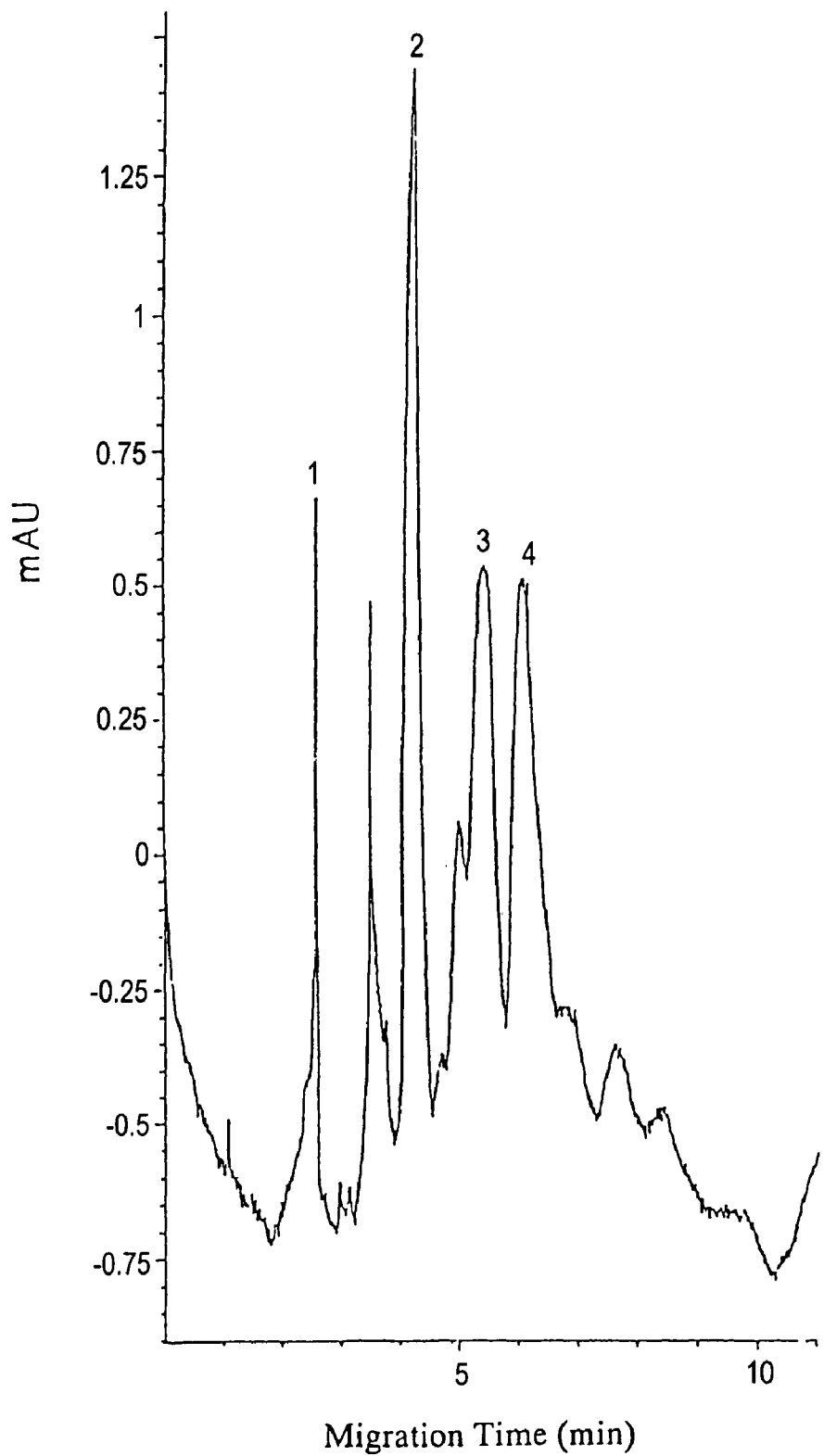

FIG. 13 shows an electrophoretic pattern obtained by capillary electrophoresis using an ordinary capillary.

Figure 14A:
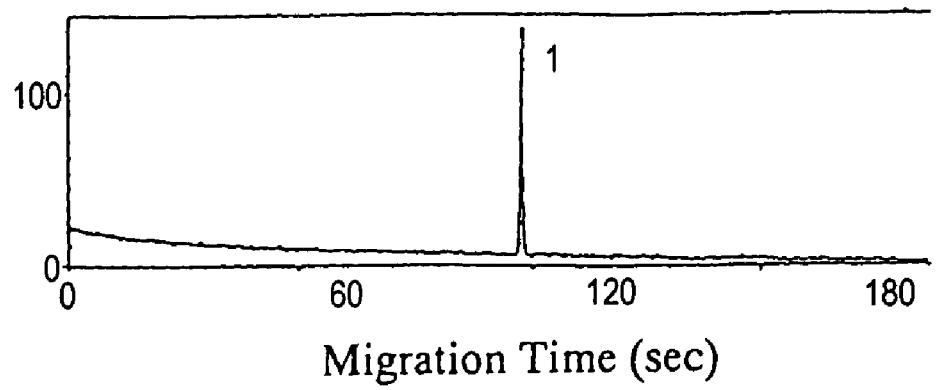
Figure 14B:
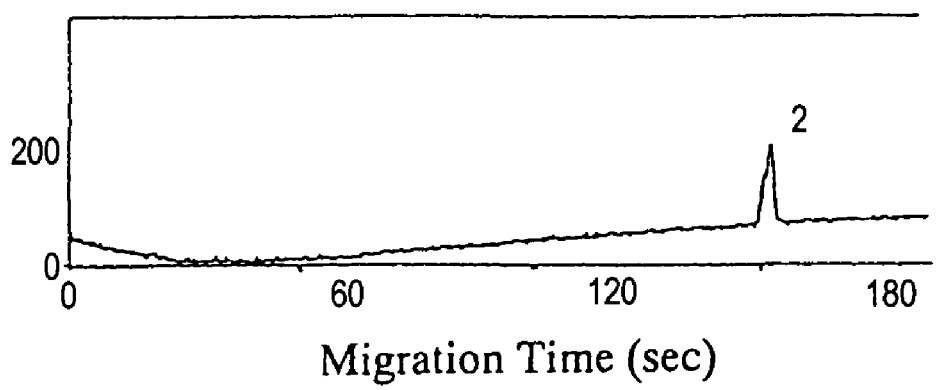
Figure 14C:
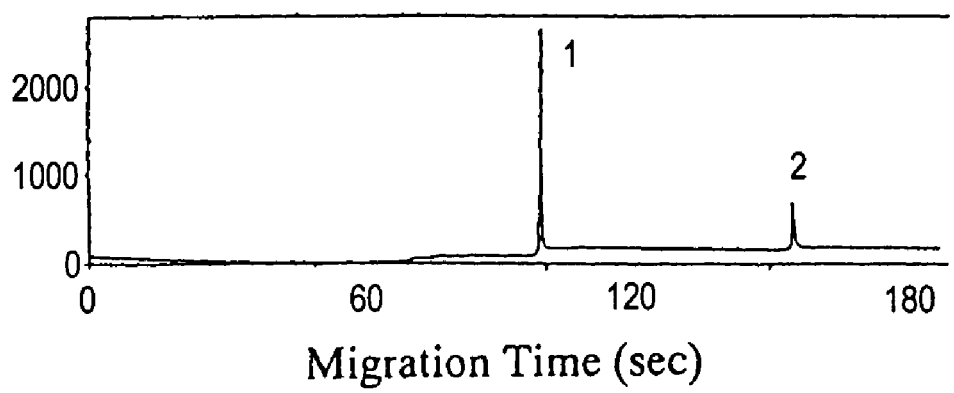

FIG. 14 shows the results obtained by subjecting two kinds of proteins to microchip electrophoresis according to the VP method. Panel A shows the results obtained when bovine insulin (MW: 5733.5) alone was electrophoresed. Panel B shows the results obtained when myogrobin (MW: 16950.9) alone was electrophoresed. Panel C shows the results obtained when both bovine insulin (MW: 5733.5) and myogrobin (MW: 16950.9) were electrophoresed.

Figure 15A:
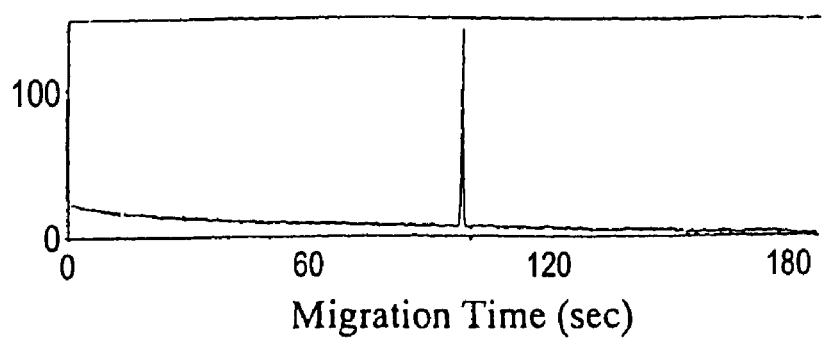
Figure 15B:
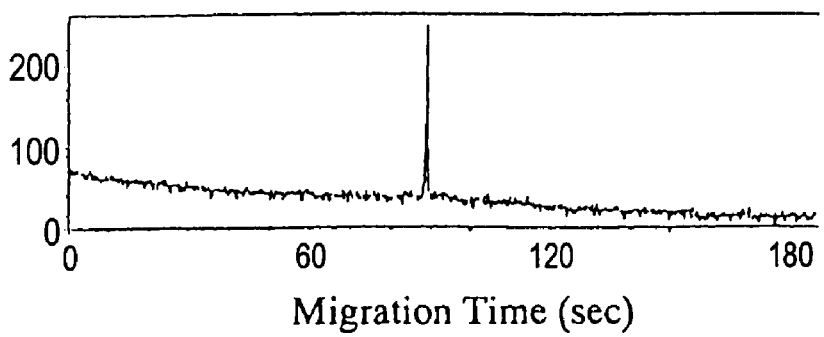
Figure 15C:
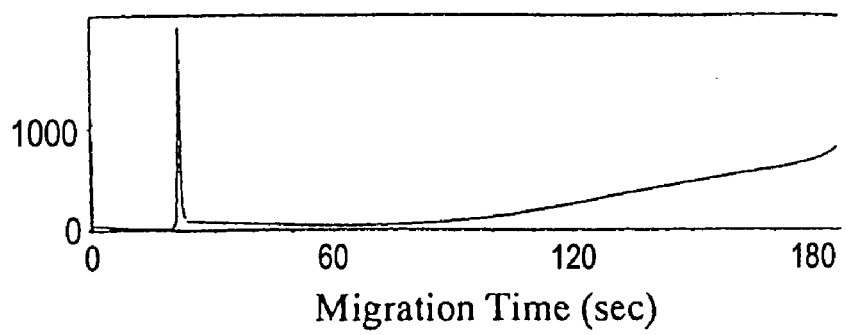

FIG. 15 shows the results of a study on the effects of pressure in a step of applying pressure prior to microchip electrophoresis in the VP method. Panel A shows the results obtained without application of pressure as in conventional microchip electrophoresis. Panel B shows the results obtained with application of low pressure (50 mbar). Panel C shows the results obtained with application of high pressure (150 mbar).

Figure 16A:
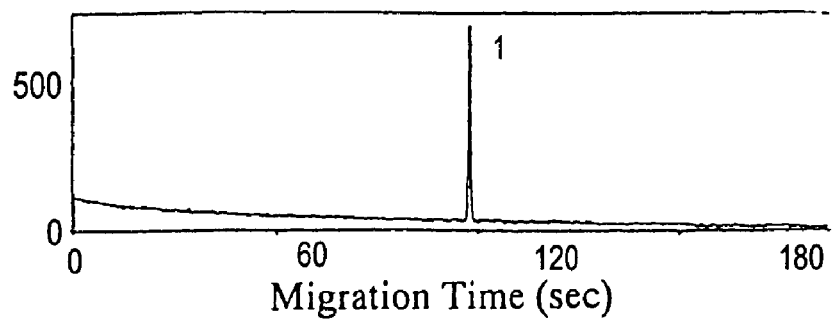
Figure 16B:
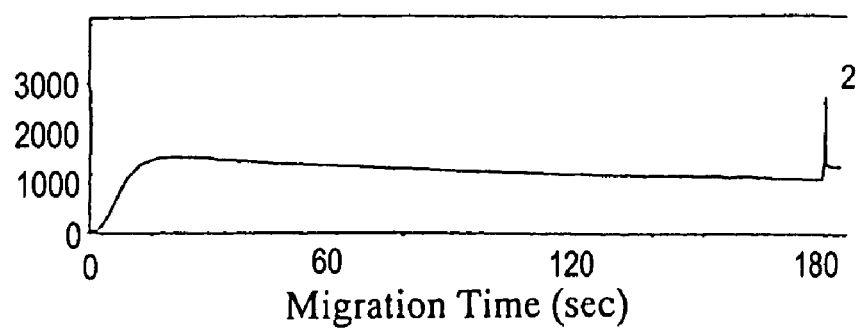
Figure 16C:
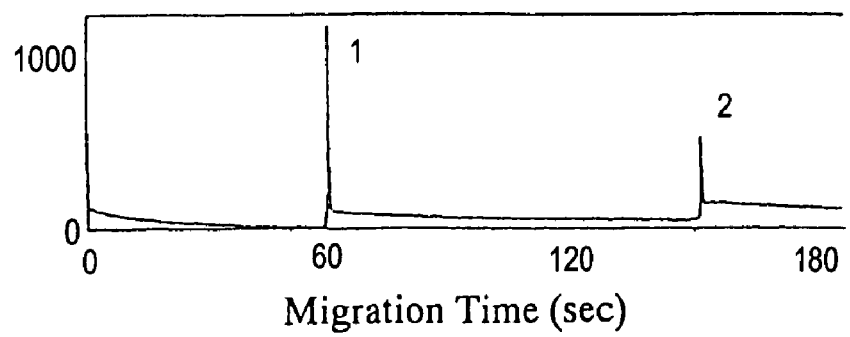

FIG. 16 shows the results obtained when bovine insulin and myosin were subjected to microchip electrophoresis by the VP method. Panels A and B show the results obtained when bovine insulin and myosin, respectively, were separated by conventional microchip electrophoresis. Panel C shows the results obtained when bovine insulin and myosin were separated by the VP method.

FIG. 17 shows the results of a study on conditions in the detection of polysaccharides [α-D(+)-galacturonic acid monohydrate, β-1,3-glucan, D-glucronic acid and seaweed extract] for each of the VP method and PP method. Panel A shows the results obtained when a voltage of 500 V (loading voltage) was applied for 20 seconds in conventional microchip electrophoresis. Panel B shows the results obtained when a voltage of 300 V (loading voltage) was applied for 10 seconds in conventional microchip electrophoresis. Panel C shows the results obtained when an electric field of 500 V (loading voltage) was applied to the loading channel, to inject the sample and thereafter a low pressure (50 mbar) was applied to the separation channel, under the conditions of no running buffer in the outlet, in the VP method. Panel D shows the results obtained when a voltage of 300 V (loading voltage) was applied to the loading channel, to inject the sample, and thereafter a low pressure (50 mbar) was applied to the separation channel, under the conditions of no running buffer in the outlet, in the VP method. Panel E shows the results obtained when a voltage of 300 V (loading voltage) was applied to the loading channel, to inject the sample and thereafter a moderate pressure (100 mbar) was applied to the separation channel, under the conditions of no running buffer in the outlet, in the VP method. Panel F shows the results obtained when a voltage of 300 V (loading voltage) was applied to the loading channel, to inject the sample and thereafter a high pressure (150 mbar) was applied to the separation channel, under the conditions of no running buffer in the outlet, in the VP method. Panel G shows the results obtained when a pressure (150 mbar) was applied to the loading channel, to inject the sample and thereafter a low pressure (50 mbar) was applied to the separation channel, under the conditions of no running buffer in the outlet, in the PP method. Panel H shows the results obtained when a pressure (150 mbar) was applied to the loading channel, to inject the sample and thereafter a high pressure (150 mbar) was applied to the separation channel, under the conditions of no running buffer in the outlet, in the PP method.

BEST MODE FOR CARRYING OUT THE INVENTION

According to the separation carrier of the present invention, it is possible to simplify the procedures, to analyze macromolecular compounds etc. at high speeds, and to obtain high resolution, in capillary electrophoresis and microchip electrophoresis.

The term macromolecular compound, as used herein, includes proteins, peptides, amino acids, sugar chains, polysaccharides, nucleic acids (e.g., DNA, RNA, etc.), etc.

The nucleic acids may be single-stranded or double-stranded.

The separation carrier of the present invention is a separation carrier for use in capillary electrophoresis or microchip electrophoresis, and one of significant features resides in that the separation carrier comprises at least one kind of compound selected from the group consisting of β-glucan and methyl cellulose.

Because the separation carrier of the present invention contains β-glucan or methyl cellulose, there are exhibited excellent effects such that the adhesion during electrophoresis of proteins, peptides, amino acids, sugar chains, polysaccharides, nucleic acids (DNA, RNA, etc.), etc. to the wall surface of the capillary used for capillary electrophoresis or the wall surface of the channel on the microchip used for microchip electrophoresis can be suppressed.

The aforementioned β-glucan may be a polysaccharide containing β-1,6 bonds or β-1,4 bonds in the side chain or main chain thereof, as long as it consists of D-glucose comprising β-glucoside bonds. The separation carrier of the present invention includes a compound or mixture containing β-1,3-glucan as a β-glucan, for example, laminaran, curdlan, plant extract, seaweed extract, yeast extract, fungal extract or culture, etc.

The β-glucan may be used alone or in combination of two or more kinds.

It is desirable, from the viewpoint of achieving high resolution and high-speed separation, that the aforementioned β-glucan have an average degree of polymerization of 2 or more, preferably 10 or more, and more preferably 20 or more. In addition, from the viewpoint of obtaining solubility, viscosity and adhesion suitable for separation, it its desirable that the β-glucan has an average degree of polymerization of 10000 or less, preferably 1000 or less, and more preferably 40 or less.

The average degree of polymerization as used herein refers to a value obtained by calculating the polymer/monomer molecular weight ratio.

β-glucan mixtures include, for example, seaweed extract; extract from mushroom such as *Agaricus, Lentinula edodes, Pleurotus osteatus, Hericium erinareum, Sparassis crispa, Shizophyllum commune* Fries and *Coriolus versicolor*; extract from plants such as barley, wild oat and oat; and extract from microorganisms such as baker's yeast, brewer's yeast, mycobacteria, fungi, filamentous fungi, Chlorella and microalgae or cultures thereof.

The aforementioned seaweed extract is obtained from a seaweed (*Undaria, Laminariales, Eisenia*, etc.) by, for example, a method described in the literature (Japanese Patent Application No. 2000-229369 etc.). Specifically, the aforementioned seaweed extract can be obtained, for example, by subjecting a seaweed (Undaria, Laminariales, Eisenia, etc.) to water extraction (extraction with hot water, warm water, cold water, ice-cooled water, etc.), acid/alkali extraction at various temperatures, dissolution in a solvent (ethanol, methanol, acetone, ether, etc.), etc.

The aforementioned seaweed extract is a mixture of, for example, water-soluble laminaran, which is a β-1,3-glucan having a large number of β-1,6 bonds, or slightly soluble laminaran, which is a β-1,3-glucan having a small number of β-1,6 bonds.

It is desirable, from the viewpoint of obtaining solubility, viscosity, and adhesion suitable for separation, that the aforementioned methyl cellulose have an average degree of polymerization of 10 or more, preferably 180 or more, and more preferably 1800 or more. In addition, it is desirable from the viewpoint of obtaining sufficient resolution that the methyl cellulose has an average degree of polymerization of 30000 or less, preferably 10000 or less, and more preferably 3000 or less.

The aforementioned methyl cellulose may be a derivative thereof. The derivatives include, for example, hydroxymethyl cellulose, hydroxymethylpropyl cellulose, hydroxypropyl cellulose, hydroxyethyl cellulose, carboxylmethyl cellulose, etc.

The separation carrier of the present invention makes it possible to simplify the procedures, to analyze macromolecular compounds, specifically, proteins, peptides, sugar chains, polysaccharides, etc., at high speeds, and obtain high resolution, in capillary electrophoresis and microchip electrophoresis, when added to the running buffer in electrophoresis.

Accordingly, the present invention provides a running buffer containing the aforementioned separation carrier.

The running buffer of the present invention is a running buffer used for capillary electrophoresis or microchip electrophoresis, and one of features resides in that the aforementioned separation carrier is contained therein.

According to such a running buffer, it is possible to suppress the adhesion during electrophoresis of analytes such as proteins, peptides, amino acids, sugar chains, polysaccharides or nucleic acids to the wall surface of the capillary used for capillary electrophoresis or the wall surface of the channel on the microchip used for microchip electrophoresis. Hence, the running buffer of the present invention enables capillary electrophoresis and microchip electrophoresis to be suitable for the migration of macromolecular compounds, to be simple in operation, and to obtain high resolution at high speeds.

The term "analyte," as used herein, refers to a substance to be analyzed contained in the sample, i.e., a macromolecular compound. The term simply referred to as "sample" means a mixture containing the macromolecular compound, etc.

It is desirable, from the viewpoint of obtaining high resolution at high speeds, that the running buffer of the present invention contains a phosphate buffer at pH 1.0 to 12.0, preferably pH 2.0 to 4.0, at a concentration of 1 mM to 0.5 M, preferably 10 mM to 0.5 M, when the analyte is a peptide.

From the viewpoint of sufficiently exhibiting an effect of resolution, the concentration of the phosphate buffer in the running buffer of the present invention is preferably 1 mM or more, more preferably 10 mM or more, still more preferably 50 mM or more, and yet more preferably 75 mM or more. In addition, from the viewpoint of exhibiting an effect of shortening migration time and obtaining high resolution, the concentration of the phosphate buffer in the running buffer of the present invention is preferably 0.5 M or less, more preferably 0.2 M or less, and still more preferably 0.1 M or less.

It is preferable, from the viewpoint of buffer capacity and resolution in electrophoresis, that the pH of the aforementioned phosphate buffer is preferably 1.0 to 12.0, more preferably 2.0 to 4.0, still more preferably 2.0 to 2.8, yet more preferably 2.5 to 2.8, and especially preferably 2.5.

When the analyte is, for example, a protein, it is desirable that the running buffer of the present invention contains a borate buffer at pH 5.0 to 11.0, preferably pH 7.0 to 9.6, at a concentration of 1 mM to 0.5 M, preferably 10 mM to 0.15 M. Here, it is preferable, from the viewpoint of sufficiently exhibiting an effect of resolution, that the concentration of the borate buffer in the running buffer of the present invention is 1 mM or more, more preferably 2.0 mM or more, still more preferably 10 mM or more, yet more preferably 20 mM or more, and especially preferably 40 mM or more, and from the viewpoint of exhibiting an effect of shortening migration time and obtaining high resolution, the concentration of the borate buffer in the running buffer of the present invention is preferably 0.5 M or less, more preferably 0.15 M or less, still more preferably 0.1 M or less, and yet more preferably 75 mM or less. It is preferable, from the viewpoint of buffer capacity and resolution in electrophoresis, that the pH of the aforementioned borate buffer is 5.0 to 11.0, more preferably 7.0 to 9.5, and still more preferably 8.0 to 9.0.

When the analyte is, for example, a sugar or polysaccharide, it is desirable that the running buffer of the present invention contains a Tris-borate buffer at pH 5.0 to 11.0, preferably pH 7.0 to 9.6, at a concentration of 1 mM to 0.5 M, preferably 10 mM to 0.5 M, and more preferably 10 mM to 0.15 M. Here, it is preferable, from the viewpoint of sufficiently exhibiting an effect of resolution, that the concentration of the Tris-borate buffer in the running buffer of the present invention is 1 mM or more, more preferably 10 mM or more, still more preferably 20 mM or more, and yet more preferably 40 mM or more, and from the viewpoint of exhibiting an effect of shortening migration time and obtaining high resolution, the concentration of the Tris-borate buffer in the running buffer of the present invention is preferably 0.5 M or less, more preferably 0.25 M or less, still more preferably 0.15 M or less, yet more preferably 0.1 M or less, and especially preferably 75 mM or less. Also, it is preferable, from the viewpoint of buffer capacity and resolution in electrophoresis, that the pH of the aforementioned Tris-borate buffer is 5.0 to 11.0, more preferably 7.0 to 9.5, still more preferably 8.0 to 9.0, and yet more preferably 8.0 to 9.0.

When the analyte is, for example, a nucleic acid, it is desirable that the above buffer comprising Tris-borate buffer at 10 mM to 0.5 M, preferably 10 mM to 0.15 M, comprises methyl cellulose at 0.001 to 0.7% by weight, preferably 0.05 to 0.7% by weight.

The concentration of the separation carrier in the running buffer comprising the separation carrier can be appropriately set according to the kind of compound used. In the case of methyl cellulose, for example, it is preferable, from the viewpoint of improvement of resolution, that the concentration of the separation carrier is 0.001 to 1.0% by weight, more preferably 0.7% by weight, still more preferably 0.05 to 0.5% by weight, and especially preferably 0.1% by weight.

When the separation carrier is curdlan, it is preferable, from the viewpoint of high-speed separation, improvement of resolution, and prevention of analyte adsorption to the wall surface, that its concentration is 0.000001 to 0.1% by weight, more preferably 0.00001 to 0.01% by weight, and still more preferably 0.0001 to 0.001% by weight.

When the separation carrier is seaweed extract, it is preferable, from the viewpoint of high-speed separation, improvement of resolution, and prevention of analyte adsorption to the wall surface, that its concentration is 0.000001 to 0.1% by weight, more preferably 0.00001 to 0.001% by weight, and especially preferably 0.0001% by weight.

According to the running buffer of the present invention, there is provided a method of electrophoresis that is based on capillary electrophoresis or microchip electrophoresis, that is suitable for the electrophoresis of macromolecular compounds, that is simple in operation, and that offers high resolution at high speeds.

The methods of electrophoresis of the present invention include, particularly the followings:

(1) a method characterized by electrophoresing a sample comprising a macromolecular compound in the presence of the aforementioned running buffer in capillary electrophoresis or microchip electrophoresis;

(2) a method of electrophoresis characterized by injecting a sample comprising a macromolecular compound to the capillary and thereafter applying pressure and electrophoresing the sample in an electric field for electrophoresis enabling the separation of the macromolecular compound, in capillary electrophoresis; and (3) a method characterized by performing in microchip electrophoresis a process comprising the following steps:

(A) using a microchip comprising a loading channel, a separation channel crossing the loading channel, a sample reservoir arranged at one end of the loading channel, and an outlet arranged at the other end of the loading channel, wherein the loading channel and the separation channel are filled with a running buffer, applying voltage or pressure to the loading channel, to supply a sample comprising macromolecular compounds from the sample reservoir, thereby introducing the sample into the separation channel [hereinafter referred to as step (A)]; and (B) applying pressure to the separation channel, and then running the sample [hereinafter referred to as step (B)].

A sample applicable to methods of electrophoresis of the present invention includes samples containing macromolecular compounds, specifically a sample comprising a protein, a peptide, an amino acid, a sugar chain, a polysaccharide, a nucleic acid (e.g., DNA, RNA, etc.), or the like. Such a "sample" includes, but is not limited to, a sample from organism.

In the case of capillary electrophoresis, it is desirable, from the viewpoint obtaining good resolution and shortening migration time, that the electric field for electrophoresis is 20 V/cm to 10 kV/cm, preferably 50 V/cm to 5 kV/cm, and more preferably 100 V/cm to 1 kV/cm.

Also, in the case of microchip electrophoresis, it is desirable, from the viewpoint of obtaining good resolution and shortening migration time, that the electric field for electrophoresis is 20 V/cm to 50 kV/cm, preferably 50 V/cm to 20 kV/cm, and more preferably 100 V/cm to 10 kV/cm.

With regard to the capillary used for the aforementioned capillary electrophoresis, inner diameter, outer diameter, total length and effective length are not particularly limited; for effective length, in particular, a capillary of short effective length can be used to enable analysis at high speeds. Here, the effective length of a capillary refers to the distance from the sample injection port to the detection portion.

In the aforementioned microchip electrophoresis, there can be used a microchip comprising a loading channel, and a separation channel crossing the loading channel, a sample reservoir arranged at one end of the loading channel and an outlet arranged at the other end of the loading channel. An example of such a microchip is shown in FIG. 11. In FIG. 11, the loading channel 2 and the separation channel 4 cross to each other on the microchip substrate 5, with the sample reservoir 1 arranged at one end of the loading channel 2 and the outlet 3 arranged at the other end.

A material for the aforementioned microchip substrate includes, for example, quartz glass, borosilicate glass, soda glass, polymethyl methacrylate, polycarbonate, dimethyl siloxane, etc. Among them, glass and polymethacrylate are desirable from the viewpoints of low adsorption of sample and easy processing of chip.

The size of the aforementioned microchip is, for example, 10 to 120 mm in length, 10 to 120 mm in width, and 500 to 5000 μm in thickness.

The shapes of the loading channel and separation channel in the aforementioned microchip are not particularly limited.

The width of the aforementioned channel can be appropriately set according to the size, purpose of use, etc. of the microchip. Specifically, it is desirable, from the viewpoint of obtaining sufficient analytical sensitivity, that the width of the aforementioned channel is 0.1 μm or more, preferably 10 μm or more. In addition, it is desirable, from the viewpoint of sufficient analytical accuracy, that the width of the aforementioned channel is 100 μm or less, preferably 50 μm or less. Also, the depth of the aforementioned channel can be appropriately set according to the size, purpose of use, etc. of the microchip; it is desirable, from the viewpoint of obtaining sufficient analytical sensitivity, that the depth of the aforementioned channel is 0.1 μm or more, preferably 10 μm or more. In addition, it is desirable, from the viewpoint of sufficient analytical accuracy, that the width of the aforementioned channel is 100 μm or less, preferably 50 μm or less. Further, although the length of the aforementioned separation channel can be appropriately set according to the size of the microchip and the compound to be analyzed, it is desirable that the effective length is longer. Effective length refers to the distance from the part in which channels are crossed, to the macromolecular compound detection point (arranged on the separation channel). It is desirable, from the viewpoint of obtaining sufficient resolution, that the effective length is 0.1 mm or more, preferably 10 mm or more. In addition, it is desirable, from the viewpoint of high-speed separation, that the effective length is 100 mm or less, preferably 50 mm or less.

Also, the size of the aforementioned reservoir can be appropriately set according to the sample volume. Specifically, it is desirable, from the viewpoints of handling during sample introduction and electrode thickness, that the diameter of the reservoir is 0.05 mm or more, preferably 1 mm or more, and it is desirable from the viewpoint of the amount of sample used that the diameter is 5 mm or less, preferably 3 mm or less.

In microchip electrophoresis, it is desirable, from the viewpoint of obtaining good resolution, that the amount (concentration) of sample injected is 0.1 ng/ml to 1 g/ml, preferably 10 ng/ml to 100 mg/ml, and more preferably 0.1 μg/ml to 10 mg/ml, when the sample is a peptide or protein. When the aforementioned sample is a sugar or polysaccharide, it is desirable, from the viewpoint of obtaining good resolution, that the amount (concentration) of sample injected is 0.1 μg/ml to 10 g/ml, preferably 1 mg/ml to 5 g/ml, and more preferably 100 mg/ml to 1 g/ml. When the aforementioned sample is a nucleic acid, it is desirable, from the viewpoint of obtaining good resolution, that the amount (concentration) of sample injected is 1 ng/ml to 500 μg/ml, preferably 10 ng/ml to 100 μg/ml, and more preferably 100 ng/ml to 50 μg/ml.

In the method of electrophoresis (1) above, running voltage etc. during electrophoresis can be appropriately set according to the compound to be analyzed [protein, peptide, amino acid, sugar chain, polysaccharide, nucleic acid (e.g., DNA, RNA, etc.), etc.]. Such running voltage can be determined according to, for example, resolution of a sample, the viscosity of the running buffer used, the number of analytes contained in the sample, etc.

The method of electrophoresis (2) above includes, particularly a method comprising performing in capillary electrophoresis a process comprising: (a) injecting a sample into a sample injection port of a capillary by application of pressure or an electrical injection, wherein the capillary comprises the sample injection port and an outlet, and the capillary is filled with a running buffer, while a voltage or a pressure applied [hereinafter referred to as step (a)], and (b) applying pressure by using water or a buffer, and thereafter running the sample [hereinafter referred to as step (b)].

Here, the running buffer includes 10 mM to 0.5 M phosphate buffer at pH 1.0 to 12.0, preferably pH 2.0 to 4.0; 10 mM to 0.5 M, preferably 10 mM to 0.15 M borate buffer at pH 5.0 to 11.0, preferably pH 7.0 to 9.5; 10 mM to 0.5 M, preferably 10 mM to 0.15 M Tris-borate buffer at pH 5.0 to 11.0, preferably pH 7.0 to 9.5; running buffers containing the separation carrier of the present invention, etc. From the viewpoint of obtaining high-speed analysis and high resolution, running buffers containing the separation carrier of the present invention are preferred.

In step (a) above, it is preferable, from the viewpoint of obtaining high-speed analysis and high resolution, that the sample is injected under the conditions of no running buffer set in the outlet of the capillary.

A means of electric injection in step (a) above includes applying an electric field suitable for sample injection in the capillary.

In step (b) above, as a means of electric injection, there may be mentioned applying a pressure suitable for shortening apparent effective length, wherein electrophoresis is performed under an running voltage suitable for the separation of macromolecular compounds in the sample. Running voltage in step (b) above can be determined according to the compound to be analyzed [protein, peptide, amino acid, sugar chain, polysaccharide, nucleic acid (e.g., DNA, RNA, etc.), etc.], resolution of a sample, the viscosity of the running buffer used, and the number of analytes contained in the sample.

The method of electrophoresis (2) above can specifically be conducted by, for example, injecting the sample to the capillary at a voltage of 1 to 30 kV, preferably 5 to 15 kV, for 1 to 30 seconds, preferably 5 to 15 seconds, in step (a), and applying pressure to water or a buffer at 2 to 50 mbar for 2 to 30 seconds and separating the analyte under an electrophoretic field of 20 V/cm to 50 kV/cm, in step (b).

Also, sample injection conditions and conditions for applying pressure can be appropriately set according to the kind and performance of apparatus, the shape of injection portion, the shape and size of sample vial, the material and shape of sample cap, sample viscosity and concentration, etc.

As the method of electrophoresis (3) above, there may specifically be mentioned a method comprising performing a process comprising applying a voltage to the loading channel under the conditions of no running buffer set in the outlet in step (A), and applying pressure to the separation channel, and then applying pressure to the loading channel and applying a voltage to the separation channel, thereby running the sample in step (B) [hereinafter referred to as process 1]; or a process comprising applying pressure to the sample reservoir, to introduce the sample comprising macromolecular compounds to the separation channel under the conditions of no running buffer set in the outlet in the step (A), and applying pressure to the separation channel, and then running the sample in the step (B) [hereinafter referred to as process 2].

According to method (3) above, there are exhibited excellent effects such that proteins having molecular weights of 9 to 205 kDa can be separated within 15 seconds, sugars having 2 to 100 constituent monosaccharides can be separated within 15 seconds, and DNA of 10 base to 10 kilobase can be separated within 50 seconds, because the method comprises the aforementioned steps.

In process 1 above, a voltage (or an electric field) suitable for the viscosities of the sample introduced and buffer used is applied in the step (A).

Specifically, a voltage of 100 to 500 V is applied to the loading channel in the step (A), and a pressure of 1 to 1520 mbar, preferably 10 to 760 mbar, is applied to the separation channel, and thereafter a voltage of 100 to 500 V is applied to the loading channel and an electric field of 20 V/cm to 50 kV/cm is applied to the separation channel in the step (B).

Resolution can be adjusted by regulating the pressure during application of pressure in the step (B).

In process 2, application of pressure in the step (A) includes pressure suitable for the viscosities of the sample to be introduced and the buffer.

Specifically, a pressure of 1 to 1520 mbar, preferably 50 to 760 mbar is applied to the sample reservoir in the step (A), and a pressure of 1 to 1520 mbar, preferably 10 to 760 mbar is applied to the separation channel and thereafter an electric field of 20 V/cm to 50 kV/cm is applied in the step (B).

Resolution can be adjusted by regulating the pressure during application of pressure in the step (B).

Therefore, it is desirable that the apparatus used for the method of electrophoresis of the present invention is equipped with an apparatus for applying pressure. The present invention encompasses electrophoresis apparatuses suitable for use in the method of electrophoresis of the present invention. Such apparatuses include, but not limited to, an apparatus comprising a capillary or microchip; a means for holding the capillary or microchip; a means for applying an electric field or a voltage to the capillary or microchip; a means for applying pressure to the capillary or microchip; a power supply for supplying an appropriate electricity to these means; a transformer; a means for regulating the electric field, voltage or pressure (computer etc.); a means for injecting a sample to the capillary or microchip; etc., and the like.

According to the method of electrophoresis of the present invention, there is provided a method for analyzing macromolecular compounds by which high resolution can be obtained simply and quickly, and which is applicable to proteome analysis, glycome analysis, etc. A great feature of such an analytical method resides in that the method comprises running a sample comprising macromolecular compounds, to separate the macromolecular compounds, and then detecting the separated macromolecular compounds, to measure their mobility.

In the analytical method of the present invention, a macromolecular compound in the sample can be detected by, for example, UV wavelength light absorption, fluorescence, laser, lamps, LED, etc., or by electrochemical measurement or chemiluminescence measurement. Specifically, when the macromolecular compound is a protein or peptide, the protein or peptide can be detected by measuring absorbance at 200 nm; by reacting SYPRO Orange and the protein or peptide, exciting at 460 to 550 nm, and determining fluorescence at 550 to 650 nm; and by electrochemical measurement, chemiluminescence measurement, etc. When the macromolecular compound is a sugar chain or polysaccharide, the sugar chain or polysaccharide can be detected by measuring absorbance at 260 nm or 280 nm; by reacting SYPRO Orange and the sugar chain or polysaccharide, and determining fluorescence; and by electrochemical measurement, chemiluminescence measurement, etc.

In the aforementioned capillary electrophoresis, for example, an apparatus capable of generating UV wavelength light and a detector for the UV wavelength light may be arranged, or an apparatus capable of generating fluorescence and a detector for the fluorescence may be arranged, in the outlet of the capillary.

In the aforementioned microchip electrophoresis, for example, a detector for UV wavelength light may be arranged, or an apparatus capable of generating fluorescence and a detector for the fluorescence may be arranged, at a detection point on the separation channel.

In the detection, when a protein, a peptide, an amino acid, a sugar chain, a polysaccharide, a nucleic acid (DNA, RNA, etc.), etc., can be achieved by UV absorption, comparison of migration time with standards, mass spectrometry, etc.

The present invention is hereinafter described in more detail by means of, but not limited to, the following examples.

PRODUCTION EXAMPLE 1

According to the method as described in the literature [e.g., Japanese Patent Application No. 2000-229369 etc.], a seaweed such as *Undaria* (including sporophyll or stem or root or frond), *Laminariales* or *Eisenia* was extracted with hot water to yield an extract.

Subsequently, the extract was dissolved in deionized water. The resulting solution was subjected to capillary electrophoresis to analyze the composition of the extract.

For the capillary electrophoresis, the HP$^{3D}$ CE system manufactured by Hewlett Packard Company was used. The capillary used was the DB-17 capillary of which inner wall was coated with diphenyl dimethyl polysiloxane [inner diameter: 0.1 mm, outer diameter: 0.36 mm, total length: 32.5 cm, effective length: 24 cm; manufactured by J&W Scientific]. Detection was carried out at 260 nm and 280 nm using a photodiode array.

The conditions for the capillary electrophoresis were capillary temperature: 25° C., electric field: 200 or 300 V/cm, injection conditions: at 5 kV for 5 seconds.

As a result, when the electric field was 300 V/cm, fraction 1 showing a maximum absorption at a wavelength of 260 nm was obtained at migration times of 3.5 to 4 minutes, and fraction 2 showing a maximum absorption at a wavelength of 280 nm was obtained at migration times of 4 to 6 minutes.

Based on comparisons with standards showed that fraction 1 above was water-soluble laminaran mainly composed of a β-1,3-glucan containing β-1,6 bonds, and fraction 2 above was a polysaccharide containing galactose or uronic acid.

EXAMPLE 1

Electrophoretic conditions in capillary electrophoresis were studied. Peptide standards manufactured by Bio-Rad Laboratories Inc. [Bardykinin (MW: 1,060), Angiotensin II (MW: 1,046), α-Melanocyte stimulating hormone (MW: 1,665), Thyrotropin releasing hormone (MW: 362), Luteinizing hormone releasing hormone (MW: 1,182), Bombesin (MW: 1,629), Leucine enkephalin (MW: 392), Methionine enkephalin (MW: 574), and Oxytocin (MW: 1,007)] were dissolved in deionized water (manufactured by ICN Biomedicals Inc.) to give a final concentration of 50 μg/ml. The solutions obtained were used as the peptide samples in the following procedures.

For the capillary electrophoresis, the $HP^{3D}$ CE system manufactured by Hewlett Packard Company was used. The capillary used was the DB-17 capillary of which inner wall was coated with diphenyl dimethyl polysiloxane [inner diameter: 0.1 mm, outer diameter: 0.36 mm, total length: 32.5 cm, coating layer thickness: 0.1 μm, manufactured by J&W Scientific]. Peptide detection was carried out with absorption at 200 nm as an index. The conditions for the capillary electrophoresis were method: CZE, electrode setting: anode-cathode, capillary temperature: 25° C., and running voltage: 10 kV. The running buffer used was 0.1 M phosphate buffer (pH 2.5).

First, conditions for sample injection and running voltage conditions for electrophoresis were studied. This investigation was conducted at 5 to 8 kV for 5 to 8 seconds for sample injection and at 5 to 15 kV for running voltage. FIG. 1 shows the results of an examination of the effects of sample injection conditions and running voltage on migration time and separation of peptides in a capillary of 24 cm in effective length.

As a result, as shown in panels D and E, it was shown that sufficient intensity was obtained with sample injection at 8 kV for 8 seconds.

It was suggested that the conditions of injecting the sample at 8 kV for 8 seconds and electrophoresing the sample at an running voltage of 10 kV may be the most suitable for obtaining a sharp peak and good resolution and shortening the migration time.

Sufficient intensity was also obtained under the conditions of injecting the sample at 5 kV for 5 seconds and electrophoresing the sample at an running voltage of 6.5 kV, or by sample injection at 8 kV for 8 seconds and electrophoresis at an running voltage of 15 kV.

Based on the above results, effective length of capillary was studied using a capillary of 24 cm or 8.5 cm in effective length. FIG. 2 shows the results of an examination of the effects of effective length of capillary on migration time and separation of peptides.

As a result, it was shown that migration time could be shortened without affecting the resolution with the use of the 24 cm capillary, even when using the capillary of 8.5 cm in effective length.

EXAMPLE 2

The migration time-shortening effect of application of pressure after sample injection was examined. Specifically, sample injection was conducted under the conditions with or without water or buffer set in the sample injection port or outlet, and thereafter sample migration time and resolution were examined without or with application of pressure (10 mbar, 8 seconds). The samples used were the peptide samples in Example 1 above. The results are shown in FIG. 3.

Panel A shows an electrophoresis pattern obtained by a conventional method (no application of pressure after sample injection). Panel B shows the results obtained under the conditions with application of pressure (10 mbar, 8 seconds) after sample injection and with phosphate buffer (pH 2.5) set in the outlet of the capillary. Panel C shows the results obtained under the conditions with application of pressure (10 mbar, 8 seconds) after sample injection and without phosphate buffer (pH 2.5) set in the outlet of the capillary.

As a result, it was shown that good resolution could be obtained and migration time could be shortened when sample injection was conducted under the conditions without buffer set in the outlet of the capillary and with application of pressure after sample injection.

Furthermore, resolution and migration time were examined when sample injection was conducted under the conditions with buffer set in the outlet of the capillary, and thereafter pressure was applied at 10 mbar for 6 to 8 seconds under the conditions with or without water or buffer set in the sample injection port or outlet. The results are shown in FIG. 4.

Panel A shows the results obtained under the conventional conditions wherein pressure is not applied after sample injection. Panels B through D show the results obtained under the conditions wherein sample injection was conducted without buffer set in the outlet of the capillary and pressure was applied with water set in the sample injection port of the capillary. Panel E shows the results obtained under the conditions wherein sample injection was conducted without buffer set in the outlet of the capillary and pressure was applied with buffer set in the sample injection port of the capillary. The respective conditions for applying pressure are shown below.

Conditions in panel B
    Sample injection followed by application of pressure at 10 mbar for 6 seconds, sample injection port: water, outlet: no buffer Conditions in panel C
    Sample injection followed by application of pressure at 10 mbar for 6 seconds, sample injection port: water, outlet: water Conditions in panel D
    Sample injection followed by application of pressure at 10 mbar for 8 seconds, sample injection port: water, outlet: buffer Conditions in panel E
    Sample injection followed by application of pressure at 10 mbar for 7 seconds, sample injection port: buffer, outlet: buffer As a result, as shown in panel D in FIG. 4, it was shown that migration time could be shortened and good resolution could be obtained under the same conditions as in panel C in FIG. 3 above.

Furthermore, the effects of time for applying pressure on migration time and resolution were examined under the conditions in panel D in FIG. 4. Some of the results are shown in FIG. 5.

The conditions for applying pressure were panel A: at 10 mbar for 2 seconds; panel B: at 10 mbar for 6 seconds; and panel D: at 10 mbar for 8 seconds.

As shown in FIG. 5, it can be seen that sharp peaks are obtained with time for applying pressures exceeding 6 seconds (7 to 8 seconds).

EXAMPLE 3

The effects of β-1,3-glucan (curdlan) on migration time and resolution were examined using a system comprising a running buffer and curdlan added thereto as a separation carrier (final concentration: 0.0001% by weight) under the conditions of conducting sample injection without phosphate buffer (pH 2.5) set in the outlet of a capillary of 8.5 cm in effective length, and thereafter applying pressure (10 mbar, 8 seconds). The samples used were the peptide samples in Example 1 above.

As a result, as shown in FIG. 6, it can be seen that sharper peaks are obtained and separation in shorter times is possible in the presence of 0.0001% by weight curdlan as a separation carrier than in the absence thereof.

Although peptide analysis takes 25 minutes using a capillary of 24 cm in effective length, the method using 0.0001% by weight curdlan as a separation carrier makes it possible to analyze peptides in 5 minutes and obtain good resolution using a capillary of 8.5 cm in effective length.

EXAMPLE 4

Running buffers suitable for protein analysis were studied by capillary electrophoresis.

Using running buffers at concentrations ranging from 0.5 to 0.1 M [phosphate buffer (pH 2.5), borate buffer (pH 5.5) or Tris-borate buffer (pH 8.5)], the optimal conditions for protein sample separation were studied.

For the capillary electrophoresis, the HP$^{3D}$ CE system manufactured by Hewlett Packard Company was used. The capillary used was the DB-17 capillary of which inner wall was coated with diphenyl dimethyl polysiloxane [inner diameter: 0.1 mm, outer diameter: 0.36 mm, total length: 32.5 cm, effective length: 24 cm; manufactured by J&W Scientific]. Peptide detection was carried out with absorption at 200 nm as an index. The conditions for the capillary electrophoresis were method: CZE, electrode setting: anode-cathode, capillary temperature: 25° C., and running voltage: 10 kV.

The samples used were the peptide samples described in Example 1.

As a result, when using phosphate buffers (pH 2.5) at concentrations of 0.1 M or less, shortened migration time and improved resolution were observed.

EXAMPLE 5

Optimal conditions for separation of protein and peptide samples were studied using as separation carriers methyl cellulose [average molecular weight: approximately 400,000, manufactured by Sigma Company], dextran [average molecular weight: approximately 100,000 to 200,000 and 60,000 to 90,000, both manufactured by Wako Pure Chemical Industries, Ltd.], curdlan [manufactured by Wako Pure Chemical Industries, Ltd.], sodium dodecyl sulfate (SDS, manufactured by Wako Pure Chemical Industries, Ltd.), sodium alginate [manufactured by Nacalai Tesque, Inc.] and the seaweed extract obtained in Production Example 1 above.

For the capillary electrophoresis, the HP$^{3D}$ CE system manufactured by Hewlett Packard Company was used. The capillary used was the DB-17 capillary of which inner wall was coated with diphenyl dimethyl polysiloxane [inner diameter: 0.1 mm, outer diameter: 0.36 mm, total length: 32.5 cm, effective length: 24 cm, manufactured by J&W Scientific]. Peptide detection was carried out with absorption at 200 nm as an index. The conditions for the capillary electrophoresis were method: CZE, electrode setting: anode-cathode, capillary temperature: 25° C., and running voltage: 10 kV. The running buffer used was 75 mM phosphate buffer (pH 2.5). The samples used were the peptide samples described in Example 1. The results are shown in FIGS. 7 through 10.

As a result, it was shown that migration time could be shortened and good resolution could be obtained by the addition of 0.1% by weight methyl cellulose (panel C in FIG. 7), by the addition of 0.0001 to 0.001% by weight curdlan (panels B and C in FIG. 8), and by the addition of 0.0001% by weight seaweed extract (panel D in FIG. 8).

EXAMPLE 6

Electrophoretic conditions in microchip electrophoresis were studied.

For the microchip electrophoresis, a microchip electrophoresis apparatus [SV1100, manufactured by Hitachi Electronics Co., Ltd.] equipped with an LED detector was used to evaluate separation of proteins in the microchip. The microchip used was the microchip in the i-chip kit developed for DNA analysis [manufactured by Hitachi Chemical Co., Ltd.]. This microchip was made from poly(methyl methacrylate) (PMMA), and comprises a loading channel of 50 μm in width, 30 μm in depth and 8 mm in length, a separation channel of 50 μm in width, 30 μm in depth and 30 mm in length, and a reservoir [see FIG. 11].

Procedures for microchip electrophoresis are described below.

1) VP Method

The aforementioned channel was filled with a buffer and a sample. Subsequently, a voltage of 10 to 500 V (loading voltage) was applied to the loading channel for 10 to 60 seconds under the conditions of no running buffer in the outlet [corresponding to 3 in FIG. 11], to inject the sample. After applying a pressure (1 to 520 mbar) to the separation channel, electrophoresis was conducted by applying a voltage of 10 to 500 V (squeezing voltage) and a voltage of 30 to 900 V (running voltage) (electric field of 100 to 300 V/cm), thereby separating the sample.

2) PP Method

Sample injection was conducted by applying a pressure (1 to 1520 mbar), in place of sample injection to the separation channel by applying a voltage, in the aforementioned VP method. After applying a pressure (1 to 1520 mbar) to the separation channel, electrophoresis was conducted by applying a voltage of 300 to 900 V (running voltage) (electric field of 100 to 300 V/cm), thereby separating the sample.

3) Conventional Microchip Electrophoresis

The aforementioned channel and well were filled with a buffer and a sample. A voltage of 100 to 500 V was applied to the loading channel for 20 seconds. Subsequently, a voltage of 100 to 500 V was applied to the crossing portion of the microchip and a voltage of 300 to 900 V (running voltage)

(electric field of 100 to 300 V/cm) was applied to the separation channel, thereby separating the sample.

(1) Protein Detection

Lysozyme (MW: 14,400), Trypsin inhibitor (MW: 21,500), Carbonic anhidrorase (MW: 31,000), Ovalbumin (MW: 45,000), Serum albumin (MW: 66,200), Phosphorylase B (MW: 97,000), β-Galactosidase (MW: 116,000), and Myosin (MW: 200,000) [all manufactured by Bio-Rad Laboratories Inc.] were used as protein standards. Each of these protein standards was dissolved in deionized water to obtain a protein solution having a final concentration of 0.3 µg to 7.5 mg/ml.

The running buffer for proteins used was 0.05 M borate buffer (pH 9.3).

In the microchip, 1 µl of SYPRO Orange was reacted with 10 µl of each protein solution. Proteins were detected by absorption at 220 nm.

The results are shown in FIG. 12. In FIG. 12, panel A shows the results obtained when a low loading voltage (100 to 300 V), for 10 to 20 seconds, and a low squeezing voltage (100 to 400 V) were applied in conventional microchip electrophoresis. Panel B shows the results obtained when a high loading voltage (500 V), for 10 to 20 seconds, and a high squeezing voltage (500 V) were applied. Panel C shows the results obtained when a loading voltage of 100 V and a squeezing voltage of 100 V were applied, and a pressure of 50 mbar was applied to the separation channel prior to electrophoresis, according to the aforementioned VP method. Panel D shows the results obtained when a mixture of eight kinds of proteins was analyzed according to the aforementioned VP method. Specifically, panel D shows the results obtained when the sample was injected to the loading channel under a pressure of 150 mbar, and thereafter a pressure of 100 mbar, followed by a squeezing voltage (100 V), was applied to the separation channel. In the panel D, the respective peaks are as follows: 1: Lysozyme, 2: Trypsin inhibitor, 3: Carbonic anhydrase, 4: Ovalbumin, 5: Serum albumin, 6: Phosphorylase, 7: β-Galactosidase, and 8: Myosin. Panel E shows the results obtained when the sample was injected to the loading channel by a pressure of 150 mbar, and thereafter a pressure of 150 mbar, followed by a squeezing voltage (100 V), was applied to the separation channel, according to the aforementioned PP method. In all cases, running voltage was 800 V (electric field of 267 V/cm).

As a result, protein peaks could not be separated in the conventional microchip electrophoresis, whereas good resolution was obtained by the aforementioned VP method and PP method.

According to the PP method shown in panel D, in particular, good detection was carried out even when the number of peaks was large, because the resolution is freely variable.

Furthermore, according to the PP method shown in panel E, 9 to 205 kDa proteins could be separated within 15 seconds.

Additionally, according to the aforementioned VP method and PP method, operating time could be shortened as compared to the separation of the same samples by capillary electrophoresis [see FIG. 13].

For the capillary electrophoresis, the HP$^{3D}$ CE system manufactured by Hewlett Packard Company was used. The capillary used was the DB-17 capillary of which inner wall was coated with diphenyl dimethyl polysiloxane [inner diameter: 0.1 mm, outer diameter: 0.36 mm, total length: 32.5 cm, effective length: 24 cm; manufactured by J&W Scientific]. Peptide detection was carried out with absorption at 200 nm as an index. The conditions for the capillary electrophoresis were method: CZE, electrode setting: anode-cathode, capillary temperature: 25° C., and running voltage: 10 kV.

(2) Effects on the Interaction of Two Kinds of Proteins in the Separation Process of Microchip Electrophoresis Using bovine insulin (MW: 5733.5) and myogrobin (MW: 16950.9) [both manufactured by Sigma Company], an electric field of 100 to 500 V (loading voltage) was applied to the loading channel under the conditions of no running buffer in the outlet [3 in FIG. 11], to inject the sample and microchip electrophoresis was conducted, according to the aforementioned VP method. The results are shown in FIG. 14.

Under these conditions, it is evident that the mobility of each of bovine insulin and myogrobin in panels A and B is the same as the mobility of each of the two kinds of proteins shown in panel C. This demonstrates that no mobility changes due to protein interaction are observed under the above conditions.

(3) Migration Time-Shortening Effect of Application of Pressure Prior to Electrophoresis in the VP Method The effects of pressure (no application of pressure, application of lower pressure, application of higher pressure) in the application of pressure process prior to electrophoresis in the aforementioned VP method were examined. The results are shown in FIG. 15.

Panel A shows the results obtained without application of pressure as in conventional microchip electrophoresis. Panel B shows the results obtained with application of lower pressure (50 mbar). Panel C shows the results obtained with application of higher pressure (150 mbar).

As a result, it was shown that migration time could be shortened by application of pressure. It was also shown that baseline disturbance was reduced with application of higher pressure (150 mbar).

(4) Separation of Two Kinds of Proteins

Bovine insulin and myosin were electrophoresed by the aforementioned VP method. The results are shown in FIG. 16.

Panels A and B show the results obtained when bovine insulin and myosin, respectively, were separated by conventional microchip electrophoresis. Panel C shows the results obtained when bovine insulin and myosin were separated by the aforementioned VP method.

Since there are no mobility changes due to protein interaction in the VP method, it was shown that the VP method could shorten the migration times of the two proteins.

(5) Polysaccharide Detection

α-D(+)-Galacturonic acid monohydrate, β-1,3-Glucan (curdlan) [both manufactured by Wako Pure Chemical Industries, Ltd.] and D-Glucuronic acid [manufactured by Nacalai Tesque, Inc.] were used as polysaccharide standards. The seaweed extract obtained by Production Example 1 above was used as the natural sample of polysaccharide. Each of these polysaccharides was dissolved in deionized water to obtain a 1 to 2 M polysaccharide solution.

The running buffer for polysaccharides used was 0.1 M Tris-borate buffer (pH 8.5). In the microchip, 1 µl of SYPRO Orange was reacted with 20 µl of each polysaccharide solution. Polysaccharides were detected by absorption at 260 nm or 280 nm.

Conditions for the detection of the aforementioned polysaccharides were studied for each of the aforementioned VP method and PP method. For control, conventional microchip electrophoresis was conducted to detect polysaccharides. The results are shown in FIG. 17.

Panel A shows the results obtained when a voltage of 500 V (loading voltage) was applied for 20 seconds in conventional microchip electrophoresis. Panel B shows the results obtained when a voltage of 300 V (loading voltage) was applied for 10 seconds in conventional microchip electrophoresis. As seen from these results, no peaks could be detected by the conventional method.

Panel C shows the results obtained when a voltage of 500 V (loading voltage) was applied to the loading channel for 20 seconds under the conditions of no running buffer in the outlet, to inject the sample and thereafter a low pressure (50 mbar) was applied to the separation channel, in the VP method.

Panel D shows the results obtained when a voltage of 300 V (loading voltage) was applied to the loading channel for 20 seconds under the conditions of no running buffer in the outlet, to inject the sample and thereafter a low pressure (50 mbar) was applied to the separation channel, in the VP method.

Panel E shows the results obtained when a voltage of 300 V (loading voltage) was applied to the loading channel for 20 seconds under the conditions of no running buffer in the outlet, to inject the sample and thereafter a moderate pressure (100 mbar) was applied to the separation channel, in the VP method.

Panel F shows the results obtained when a voltage of 300 V (loading voltage) was applied to the loading channel for 20 seconds under the conditions of no running buffer in the outlet, to inject the sample and thereafter a high pressure (150 mbar) was applied to the separation channel, in the VP method.

Panel G shows the results obtained when a pressure (150 mbar) was applied to the loading channel under the conditions of no running buffer in the outlet, to inject the sample and thereafter a low pressure (50 mbar) was applied to the separation channel, in the PP method.

Panel H shows the results obtained when a pressure (150 mbar) was applied to the loading channel under the conditions of no running buffer in the outlet, to inject the sample and thereafter a high pressure (50 mbar) was applied to the separation channel, in the PP method.

In all cases, running voltage was 800 V (electric field of 267 V/cm). As a result, it was shown that migration time could be further shortened and good resolution could be obtained under the conditions in panel H.

(6) DNA Detection

Solutions of 0.1 µg to 500 µg/µl DNA [ladder of 10 kb in size (manufactured by Funakoshi)] were used as the samples. A solution comprising 0.01 to 1.0% by weight methyl cellulose contained in a buffer comprising 10 mM to 0.15 M Tris-borate buffer (pH 7.0 to 10.0) was used as the running buffer, and microchip electrophoresis was conducted according to the VP method and PP method in (5) above.

As a result, it was shown that migration time was at least 170 seconds for 10 kilobases in conventional microchip electrophoresis, whereas migration time could be shortened to about 50 seconds and good resolution could be obtained according to the VP method and PP method.

INDUSTRIAL APPLICABILITY

According to the method of electrophoresis and the method for analyzing macromolecular compound of the present invention, it is possible to achieve high resolution quickly. Therefore, the methods are useful in the High Through-put screening analysis of proteins or sugar chains in gene analysis, proteome analysis or glycome analysis, and are expected to be applied in medical diagnostic apparatuses and the elucidation of biological functions, mechanisms of onset of diseases, etc.

The invention claimed is:

1. A method of electrophoresis for a sample comprising macromolecular compounds comprising the steps:
    (a) injecting a sample into a sample injection port of a capillary of an apparatus for capillary electrophoresis by application of pressure or an electrical injection,
    wherein the apparatus comprises the sample injection port, the capillary and an outlet, and the capillary is filled with a running buffer,
    where no water or no running buffer is set in the outlet of the apparatus when the sample is injected; and
    (b) applying pressure to the running buffer and then running the sample in capillary electrophoresis.

2. The method of electrophoresis according to claim 1, wherein the macromolecular compounds are one kind selected from the group consisting of a protein, a peptide, an amino acid, a sugar chain, a polysaccharide and a nucleic acid.

3. The method of electrophoresis according to claim 1, wherein the sample is injected into the capillary by an electrical injection at 1 to 30 kV for 1 to 30 seconds in the step (a), and
    wherein the sample is run in an electric field for electrophoresis of 20 V/cm to 10 kV/cm in the step (b).

4. The method of electrophoresis according to claim 1, wherein the sample is injected into the capillary by an electrical injection at 1 to 30 kV for 1 to 60 seconds in the step (a), and
    wherein a pressure of 2 to 50 mbar is applied for 2 to 30 seconds in the step (b).

5. The method of electrophoresis according to claim 1, wherein the running buffer comprises a separation carrier composed of one kind of compound selected from the group consisting of β-glucan and methyl cellulose.

6. The method of electrophoresis according to claim 5, wherein the separation carrier comprises as the β-glucan at least one kind selected from the group consisting of laminaran containing β-1,3-glucan, curdlan containing β-1,3-glucan, a plant extract containing β-1,3-glucan, a seaweed extract containing, β-1,3-glucan, a yeast extract containing β1,3-glucan, a fungal extract containing β-1,3-glucan, and a fungal cultured medium containing β-1,3-glucan.

7. The method of electrophoresis according to claim 5, wherein the separation carrier comprises a seaweed extract containing β-1,3-glucan as the β-glucan.

8. The method of electrophoresis according to claim 7, wherein the seaweed extract is an extract obtained by subjecting raw material seaweed to one kind of extraction method selected from the group consisting of a water extraction, an acid/alkali extraction and a solvent extraction.

9. The method of electrophoresis according to claim 5, wherein the running buffer is usable for capillary electrophoresis or microchip electrophoresis, and the running buffer comprises the separation carrier.

10. The method of electrophoresis according to claim 5, wherein the running buffer is one kind of buffer selected from the group consisting of the following (1) to (3):
    (1) a buffer comprising a phosphate buffer at pH 1.0 to 12.0 at a concentration of 1 mM to 0.5 M;
    (2) a buffer comprising a borate buffer at pH 5.0 to 1.0 at a concentration of 1 mM to 0.5 M; and
    (3) a buffer comprising a tris-borate buffer at pH 5.0 to 1.0 at a concentration of 1 mM to 0.5 M, and wherein the running buffer comprises methyl cellulose at a concentration of 0.001 to 0.5% by weight.

11. The method of electrophoresis according to claim 5, wherein the running buffer is one kind of buffer selected from the group consisting of the following (1) to (4):
   (1) a buffer comprising a phosphate buffer at pH 1.0 to 12.0 at a concentration of 1 mM to 0.5 M;
   (2) a buffer comprising a borate buffer at pH 5.0 to 1.0 at a concentration of 1 mM to 0.5 M;
   (3) a buffer comprising a tris-borate buffer at pH 5.0 to 1.0 at a concentration of 1 mM to 0.5 M; and
   (4) a buffer further comprising 0.001 to 1.0% by weight of methyl cellulose in the buffer of the above item (3),
and wherein the running buffer comprises curdlan at a concentration of 0.000001 to 0.1% by weight.

12. The method of electrophoresis according to claim 5, wherein the running buffer is one kind of buffer selected from the group consisting of the following (1) to (4):
   (1) a buffer comprising a phosphate buffer at pH 1.0 to 12.0 at a concentration of 1 mM to 0.5 M;
   (2) a buffer comprising a borate buffer at pH 5.0 to 1.0 at a concentration of 1 mM to 0.5 M;
   (3) a buffer comprising a tris-borate buffer at pH 5.0 to 1.0 at a concentration of 1 mM to 0.5 M; and
   (4) a buffer further comprising 0.001 to 1.0% by weight of methyl cellulose in the buffer of the above item (3),
   and wherein the running buffer comprises a seaweed extract at a concentration of 0.000001 to 0.1% by weight.

13. A method of electrophoresis, comprising the steps:
   (A) using a microchip comprising a loading channel, a separation channel crossing the loading channel, a sample reservoir arranged at one end of the loading channel, and an outlet arranged at the other end of the loading channel, wherein the loading channel and the separation channel are filled with a running buffer, applying voltage or pressure to the loading channel, to supply a sample comprising macromolecular compounds from the sample reservoir, thereby introducing the sample into the separation channel,
   where no running buffer is set in the outlet when the sample is introduced into the separation channel; and
   (B) applying pressure to the separation channel, and then running the sample,
   wherein voltage is applied to the loading channel and the separation channel, thereby running the sample, in the step (B).

14. The method of electrophoresis according to claim 13, wherein the macromolecular compounds are one kind selected from the group consisting of a protein, a peptide, an amino acid, a sugar chain, a polysaccharide and a nucleic acid.

15. The method of electrophoresis according to claim 13, wherein resolution is adjusted by controlling a degree of pressure applied in the step (B).

16. The method of electrophoresis according to claim 13, wherein a voltage of 10 to 500 V (loading voltage) is applied to the loading channel for 2 to 60 seconds in the step (A); and a voltage of 10 to 500 V (squeezing voltage) is applied to the loading channel and, an electric field of 20 V/cm to 50 kV/cm is applied to the separation channel in the step (B).

17. The method of electrophoresis according to claim 13, wherein the sample is introduced into the separation channel by applying pressure to the sample reservoir under the conditions of no running buffer set in the outlet in the step (A); and
   wherein pressure is applied to the separation channel and then the sample is run in the step (B).

18. The method of electrophoresis according to claim 17, wherein a pressure of 1 to 1520 mbar is applied to the sample reservoir in the step (A); and
   wherein a pressure of 1 to 1520 mbar is applied to the separation channel, and then an electric field of 20 V/cm to 50 kV/cm is applied thereto, in the step (B).

19. The method of electrophoresis according to claim 13, wherein proteins having molecular weights of 9 to 205 kDa are separated within 15 seconds.

20. The method of electrophoresis according to claim 13, wherein sugars comprising 2 to 100 monosaccharides as a constitutive sacccharide are separated within 15 seconds.

21. The method of electrophoresis according to claim 13, wherein nucleic acids of 10 bases to 10 kilobases are separated within 50 seconds.

22. A method for analyzing macromolecular compounds, characterized by comprising the steps of running a sample comprising macromolecular compounds by the method of electrophoresis of any one of claims 1 or 13, thereby separating the macromolecular compounds; and measuring mobility by detecting the separated macromolecular compounds.

23. The method for analyzing macromolecular compounds according to claim 22, wherein the macromolecular compounds are one kind selected from the group consisting of a protein, a peptide, an amino acid, a sugar chain, a polysaccharide and a nucleic acid.

24. The method for analyzing macromolecular compounds according to claim 22, wherein the separated macromolecular compounds are detected by at least one means selected from the group consisting of a determination of UV wavelength light absorption, a fluorescence detection, an electrochemical detection and a chemiluminescence detection.

25. A method of electrophoresis for a sample comprising macromolecular compounds comprising the steps:
   (a) injecting a sample into a sample injection port of a capillary of an apparatus for capillary electrophoresis by application of pressure or an electrical injection, the capillary having been filled with a buffer, wherein
   the apparatus comprises the sample injection port, the capillary and an outlet, and
   no water or no buffer is set at the outlet; and
   (b) applying pressure t the buffer so as to run the sample in capillary electrophoresis.

* * * * *